US006180679B1

(12) United States Patent
Shih et al.

(10) Patent No.: US 6,180,679 B1
(45) Date of Patent: Jan. 30, 2001

(54) METHOD FOR TREATING FUNGAL INFECTIONS

(75) Inventors: Chuan Shih, Carmel; Daniel Charles Williams, Fishers, both of IN (US)

(73) Assignee: Eli Lilly and Company, Indianapolis, IN (US)

( * ) Notice: Under 35 U.S.C. 154(b), the term of this patent shall be extended for 0 days.

(21) Appl. No.: 09/367,236

(22) PCT Filed: Apr. 7, 1998

(86) PCT No.: PCT/US98/07269

§ 371 Date: Oct. 20, 1999

§ 102(e) Date: Oct. 20, 1999

(87) PCT Pub. No.: WO98/46221

PCT Pub. Date: Oct. 22, 1998

(51) Int. Cl.[7] ........................ A61K 31/165; A61K 38/00; A61K 31/70; A61K 31/16

(52) U.S. Cl. ................................ 514/619; 514/9; 514/11; 514/30; 514/616; 514/617

(58) Field of Search .................................. 514/9, 11, 31, 514/617, 619, 616

(56) References Cited

U.S. PATENT DOCUMENTS 4,845,085 * 7/1989 Sesin .................................... 514/183
4,845,086 * 7/1989 Sesin .................................... 514/183
4,868,208 * 9/1989 Sesin et al. .......................... 514/475
4,946,835 * 8/1990 Hirsch et al. ........................ 514/183
6,013,626 * 1/2000 Moore et al. ........................... 514/9

FOREIGN PATENT DOCUMENTS

WO
PCT9708334 * 3/1997 (WO) .
PCT9808506 * 3/1998 (WO) .

* cited by examiner

*Primary Examiner*—Frederick Krass
*Assistant Examiner*—Donna Jagoe
(74) *Attorney, Agent, or Firm*—John H. Engelmann

(57) ABSTRACT

The present invention provides a method for controlling fungal growth, mycotic infections, yeast infections and parasitic infections using a therapeutically effective amount of a compound selected from Compounds (I-V). Further provided is a method for providing mdr inhibition using a therapeutically effective amount of a compound of formula (IA). Also provided is an antifungal composition comprising at least five percent (5%) by weight of a compound selected from Compounds (I-V).

33 Claims, No Drawings

METHOD FOR TREATING FUNGAL INFECTIONS

This application is a 371 of PCT/US98/07269 filed on Apr. 7, 1998.

BACKGROUND OF THE INVENTION

This invention relates to the fields of pharmaceutical and organic chemistry and provides cryptophycin compounds useful for treating fungal infections.

The incidence of serious, life-threatening, fungal infections is increasing at an alarming rate. The number of *Candida albicans* bloodstream infections in non-teaching hospitals increased by 370% between 1980 and 1990. At the same time the incidence of bloodstream infections by *C. albicans* in teaching hospitals increased by 487% in the same time period. With the exception of coagulase negative staphylococci, statistically, *C. albicans* represents the fastest growing area of concern in hospital acquired bloodstream infections (Banerjee et al., 1991, *American Journal of Medicine* 91 (3B): 86S–89S).

The rising incidence of nosocomial fungal infections is being fueled by changing medical practices, including invasive surgical procedures addressing such problems as joint replacement and open heart surgery, increased use of cancer chemotherapy, and the AIDS epidemic. All of these processes compromise the immune system and provide an environment in which fungal infections can be established.

Unfortunately, the diagnosis of fungal infections is difficult and time consuming. Rather than waiting for the results of diagnostic tests, empirical antifungal therapy must frequently be initiated with a compound such as amphotericin B (which may have safety/toxicity issues) or one of the azoles to which fungal species are developing resistance. Thus, having an antifungal with a broad spectrum of activity coupled with a low toxicity profile would be very desirable.

Further, the existence of multiple drug resistance (mdr)-related genes in a non-pathological as well as in key opportunistic pathological fungi has been discovered. These genes have been termed "mdr-like" because of the homology that exists between the proteins encoded by these genes and the human mdr-1 gene product.

With the discovery of mdr-like genes in a variety of fungi, including key pathogenic fungi, such as *Aspergillus flavus, Aspergillus fumigatus* and *Cryptococcus neoformans* the prospect of discovering an antifungal agent that can have fungal mdr inhibitor activity becomes extraordinarily desirable.

Applicants have discovered agents which can be useful antifungal agents. Two particularly desired compounds are known as Cryptophycin 52 and Cryptophycin 55.

Further, Applicants provide compounds which can provide useful mdr inhibitor activity.

SUMMARY OF THE INVENTION

The presently claimed invention provides a method for controlling fungal growth comprising administering a therapeutically effective amount of a compound selected from the group consisting of Compound I, Compound II, Compound III, Compound IV and Compound V.

Compound I:

I

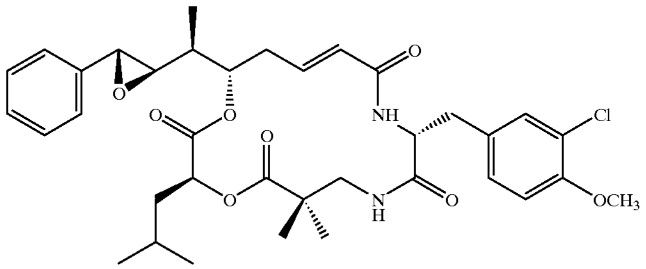

Compound II:

II

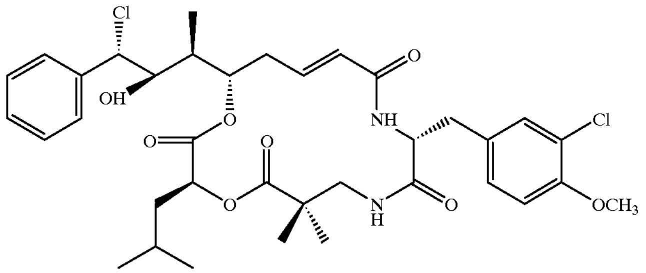

-continued

Compound III:

III

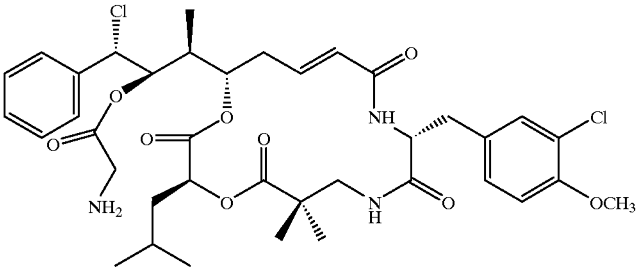

Compound IV:

IV

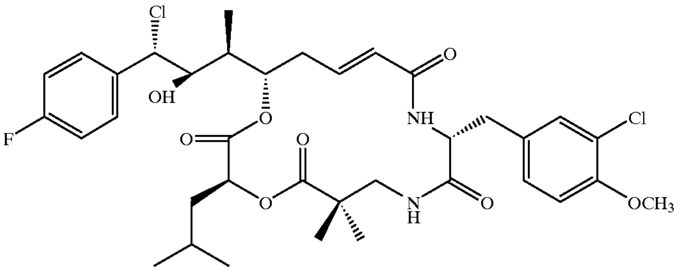

Compound V:

V

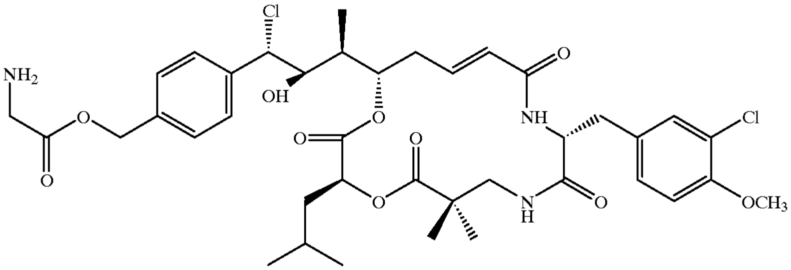

or a pharmaceutically acceptable salt thereof.

The presently claimed invention provides a method for providing mdr inhibitor activity comprising administering a therapeutically effective amount of a compound of the formula:

IA

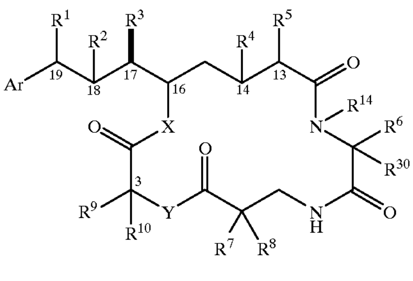

wherein

Ar is phenyl or any simple unsubstituted or substituted aromatic or heteroaromatic group;

$R^1$ is halogen, SH, amino, monoalkylamino, dialkylamino, trialkylammonium, alkylthio, dialkylsulfonium, sulfate, or phosphate;

$R^2$ is OH or SH; or $R^1$ and $R^2$ may be taken together to form an epoxide ring, and aziridine ring, an episulfide ring, a sulfate ring, or monoalkylphosphate ring; or $R^1$ and $R^2$ may be taken together to form a second bond between $C_{18}$ and $C_{19}$;

$R^3$ is a lower alkyl group;

$R^4$ is H;

$R^5$ is H;

$R^4$ and $R^5$ may be taken together to form a second bond between $C_{13}$ and $C_{14}$;

$R^6$ is benzyl, hydroxybenzyl, alkoxybenzyl, halohydroxybenzyl, dihalohydroxybenzyl, haloalkoxybenzyl, or dihaloalkoxybenzyl group, a substituent selected from the group consisting of B-ring heteroaromatic, substituted heteroaromatic, B-ring ($C_1$–$C_6$)alkyl, ($C_3$–$C_8$)cycloalkyl, substituted $C_3$–$C_8$ cycloalkyl, substituted ($C_1$–C6)alkyl, a group of the formula III':

III'

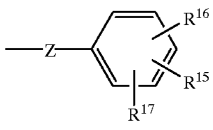

and a group of the formula III″:

-continued

III″

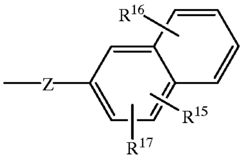

;

$R^7$ is H or a lower alkyl group;

$R^8$ is H or a lower alkyl group;

$R^9$ is H or a lower alkyl group;

$R^{10}$ is H or a lower alkyl group;

$R^{14}$ is H or a lower alkyl group;

$R^{15}$, $R^{16}$, and $R^{17}$ are each independently selected from the group consisting of hydrogen, $OR^{18}$, halo, $NH_2$, $NO_2$, $OPO_4H_2$, $OR^{19}$phenyl, and ZZ;

$R^{18}$ is $C_1$–$C_6$ alkyl;

$R^{19}$ is $C_1$–$C_6$ alkyl;

$R^{30}$ is $C_1$–$C_6$ alkyl;

n is 0, 1, or 2;

p is 0, 1, or 2;

m is 0, 1, or 2;

X is O, $NH^-$ or alkylamino;

Y is C, O, NH, S, SO, $SO_2$ or alkylamino;

Z is selected from the group consisting of $—(CH_2)_n—$, $—(CH_2)_p—O—(CH_2)_m—$ and $(C_3–C_5)$cycloalkyl;

ZZ is selected from the group consisting of a simple substituted aromatic group and a simple unsubstituted aromatic group; or a pharmaceutically acceptable salt or solvate thereof. The compounds of formula IA are disclosed in PCT International Publication Number WO 96/40184, published Dec. 19, 1996. The compounds of formula IA also include to known cryptophycin compounds such as Cryptophycin 1, 3, 5, 13, 15. Such cryptophycin compounds are disclosed in U.S. Pat. Nos. 4,946,835, 4,845,085, 4,845,086, and 4,868,208, which are hereby incorporated by reference. The term shall also refer to other known cryptophycin compounds such as cryptophycin 8.

The present invention provides an antifungal composition comprising at least five percent (5%) by weight of a compound selected from the group consisting of Compound I, Compound II, Compound III, Compound IV and Compound V in admixture with one or more pharmaceutically acceptable carriers or excipients therefor.

The present invention further provides a method for controlling a mycotic infection comprising administering a therapeutically effective amount of a compound selected from the group consisting of Compound I, Compound II, Compound III, Compound IV and Compound V. Additionally, the present invention provides a method for controlling a yeast infection comprising administering a therapeutically effective amount of a compound selected from the group consisting of Compound I, Compound II, Compound III, Compound IV and Compound V. Finally, the present invention provides a method for controlling a parasitic infection comprising administering a therapeutically effective amount of a compound selected from the group consisting of Compound I, Compound II, Compound III, Compound IV and Compound V.

DETAILED DESCRIPTION OF THE INVENTION

As used herein, the term "simple alkyl" shall refer to $C_1$–$C_7$ alkyl wherein the alkyl may be saturated, unsaturated, branched, or straight chain. Examples include, but are in no way limited to, methyl, ethyl, n-propyl, isopropyl, n-butyl, propenyl, sec-butyl, n-pentyl, isobutyl, tert-butyl, sec-butyl, methylated butyl groups, pentyl, tert pentyl, sec-pentyl, methylated pentyl groups and the like.

As used herein, the term "B-ring $C_1$–$C_6$ alkyl" refers to saturated, unsaturated, branched and straight chain alkyl wherein the B-ring $C_1$–$C_6$alkyl group may include up to three (3) non-carbon substituents. Such non-carbon substituents are most preferredly selected from the group consisting of OH, $SCH_2$phenyl, $NH_2$, CO, $CONH_2$, $CO_2H$, $PO_3H_2$, $SO_2R^{21}$ wherein $R^{21}$ is selected from hydrogen and $C_1$–$C_3$ alkyl.

As used herein, the term "substituted phenyl" shall refer to a phenyl group with from one to three non-hydrocarbon substituents which may be independently selected from the group consisting of simple alkyl, Cl, Br, F, and I.

As used herein, the term "substituted benzyl" shall refer to a benzyl group with from one to three non-hydrocarbon substitutents which may be independently selected from the group consisting of simple alkyl, Cl, Br, F, and I wherein such substituents may be attached at any available carbon atom.

As used herein "B-ring heterocyclic group" refers to aromatic rings which contain one or more non-carbon substituent selected from the group consisting of oxygen, nitrogen, and sulfur. Especially preferred B-ring heterocyclic groups are selected from, but not limited to, the group consisting of:

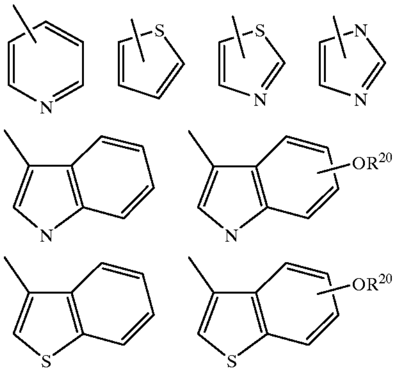

$R^{20}$ is selected from hydrogen and $C_1$–$C_6$ alkyl.

As used herein "cycloalkyl" refers to a saturated C—C cycloalkyl group wherein such group may include from zero to three substituents selected from the group consisting of $C_1$–$C_3$ alkyl, halo, and $OR^{22}$ wherein $R^{22}$ is selected from hydrogen and $C_1$–$C_3$ alkyl. Such substituents may be attached at any available carbon atom. It is especially preferred that cycloalkyl refers to substituted or unsubstituted cyclohexyl.

As used herein "Lower alkoxyl group" means any alkyl group of one to five carbon atoms bonded to an oxygen atom. As used herein "lower alkyl group" means an alkyl group of one to five carbons and includes linear and nonlinear hydrocarbon chains, including for example, but not limited to, methyl, ethyl, propyl, isopropyl, butyl, isobutyl, tert-butyl, sec-butyl, methylated butyl groups, pentyl, tert pentyl, sec-pentyl, and methylated pentyl groups. As used herein "allylically substituted alkene" means any alkene having from one to seven carbon atoms which contains an alkyl substitution on it.

As used herein "epoxide ring" means a three-membered ring whose backbone consists of two carbons and an oxygen atom. As used herein, "aziridine ring" means a three-membered ring whose backbone consists of two carbon atoms and a nitrogen atom. As used herein "sulfide ring" means a three-membered ring whose backbone consists of two carbon atoms and a sulfur atom. As used herein "episulfide ring" means a three-membered ring whose backbone consists of two carbon and a sulfur atom. As used herein "sulfate group" means a five membered ring consisting of a carbon-carbon-oxygen-sulfur-oxygen backbone with two additional oxygen atoms connected to the sulfur atom. As used herein, "monalkylphosphate ring" means a five membered ring consisting of a carbon-carbon-oxygen-phosphorous-oxygen backbone with two additional oxygen atoms, one of which bears a lower alkyl group, connected to the phosphorous atom.

As used herein, "simple unsubstituted aromatic group" refers to common aromatic rings having 4n+2 electrons in a moncyclic conjugated system, for example, but not limited to: furyl, pyrrolyl, thienyl, pyridyl and the like, or a bicyclic conjugated system, for example but not limited to indolyl or naphthyl.

As used herein "simple substituted aromatic group" refers to a phenyl group substituted with a single group selected from the group consisting of halogen and lower alkyl group.

As used herein, "heteroaromatic group" refers to aromatic rings which contain one or more non-carbon substituent selected from the group consisting of oxygen, nitrogen, and sulfur.

As used herein, "halogen" refers to those members of the group on the periodic table historically known as halogens, for example, F, Cl, Br or I. Methods of halogenation include, but are not limited to, the addition of hydrogen halides, substitution at high temperature, photohalogenation, etc., and such methods are known to the skilled artisan.

As used herein, the term "mammal" shall refer to the Mammalia class of higher vertebrates. The term "mammal" includes, but is not limited to, mice, dogs, rats, hamsters, guinea pigs, cows, apes and humans. The term "treating" as used herein includes prophylaxis of the named condition or amelioration or elimination of the condition once it has been established. The cryptophycin compounds claimed herein can be useful for veterinary health purposes as well as for the treatment of a human patient.

As used herein, the term "therapeutically effective amount refers to an amount of Compound I, Compound II, Compound III, Compound IV, or Compound V which is effective, upon single or multiple dose administration or continuous infusion to the patient, in controlling fungal growth, in controlling a mycotic infection, in controlling a yeast infection or in controlling a parasitic infection. The term "therapeutically effective amount also refers to an amount of a compound of formula IA which is effective in is providing mdr inhibitor activity in a patient in need thereof. As used herein the term "controlling" as referring to fungal growth, eycotic infection, yeast infection or parasitic infection refers to slowing, interrupting, arresting or stopping of the spread of the given infection and does not necessarily refer to a total elimination of the infection.

A therapeutically effective amount can be readily determined by the attending diagnostician, as one skilled in the art, by the use of known techniques and by observing results obtained under analogous circumstances. In determining the therapeutically effective amount or dose, a number of factors are considered by the attending diagnostician, including, but not limited to: the species of mammal; its size, age, and general health; the specific disease involved; the degree of or involvement or the severity of the disease; the response of the individual mammal; the particular compound administered; the bioavailability characteristics of the preparation administered; the dose regimen selected; the use of concomitant medication; and other relevant circumstances.

A therapeutically effective amount of radiation therapy can be readily determined by one of ordinary skill in the art. A therapeutically effective amount of a compound selected from Compounds I-V or a compound of formula IA compound is expected to vary from about 0.001 milligram per kilogram of body weight per day (mg/kg/day) to about 1000 mg/kg/day. Preferred amounts are expected to vary from about 0.01 to about 10 mg/kg/day.

A compound of Compounds I-V or a compound of formula IA can be administered to the mammal in any form or mode which makes the compound bioavailable in effective amounts, including oral and parenteral routes. For example, a compound of Compounds I-V or a compound of formula IA can be administered orally, subcutaneously, intramuscularly, intravenously, transdermally, intranasally, rectally, and the like. Oral, intravenous or intramuscular administration is generally preferred. One skilled in the art of preparing formulations can readily select the proper form and mode of administration depending upon the particular characteristics of the compound selected, the disease state to be treated, the stage of the disease, and other relevant cicumstances.

The compounds can be administered alone or in the form of a pharmaceutical composition in combination with pharmaceutically acceptable carriers or excipients, the proportion and nature of which are determined by the solubility and chemical properties of the compound selected, the chosen route of administration, and standard pharmaceutical practice. The compounds of the invention, while effective themselves, may be formulated and administered, where appropriate, in the form of their pharmaceutically acceptable acid addition salts for purposes of stability, convenience of crystallization, increased solubility and the like Compounds of this invention have been found to be useful against pathogenic fungi. Example of pathogenic fungi include, but are not limited to, *Cryptococcus neoformans, Candida albicans, Coccidiodes immitis, Histoplasma capsulatum, Asperfillus fumigatus, Blastomyces dermatitidis,* and *Rhizopus arrhizus*. For example, the usefulness for treating *Cryptococcus neoformans* can be illustrated with test results against *Cryptococcus neoformans* employing yeast nitrogen base detrose agar medium. In carrying out the assay, a compound of this invention is solubilized in dimethyl sulfoxide supplemented with Tween 20. Twofold dilutions are made with sterile distilled water/10 percent DMSO to obtain final drug concentrations in the agar dilution assay plates ranging from 0.008 $\mu$g/ml to 16.0 $\mu$g/ml against an expanded panel of 84 *Cryptococcus neoformans* strains. The minimum inhibitory concentration against the panel of 84 *Cryptococcus neoformans* isolates is determined to illustrate the desired antifungal activity.

These compounds and compositions can be administered to mammals for veterinary use. For example, domestic animals can be treated in much the same way as a human clinical patient. In general, the dosage required for therapeutic effect will vary according to the type of use, mode of administration, as well as the particularized requirements of the individual hosts. Typically, dosages will range from about 0.001 to 1000 mg/kg, and more usually 0.01 to 10 mg/kg of the host body weight. Alternatively, dosages within these ranges can be administered by constant infusion over an extended period of time, usually exceeding 24 hours, until the desired therapeutic benefits are obtained. Indeed, drug dosage, as well as route of administration, must be selected on the basis of relative effectiveness, relative toxicity, growth characteristics of tumor and effect of Formula I compound on cell cycle, drug pharmacokinetics, age, sex, physical condition of the patient and prior treatment.

The compounds of this invention, with or without additional anti-fungal agents, may be formulated into therapeutic compositions as natural or salt forms. Pharmaceutically acceptable non-toxic salts include base addition salts which may be derived from inorganic bases such as for example, sodium, potassium, ammonium, calcium, or ferric hydroxides, and such organic bases as isopropylamine, trimethylamine, 2-ethylamino ethanol, histidine, procaine, and the like. Such salts may also be formed as acid addition salts with any free cationic groups and will generally be formed with inorganic acids such as for example, hydrochloric or phosphoric acids or organic acids such as acetic, oxalic, tartaric, mandelic, and the like. Additional excipients which further the invention are provided to the skilled artisan for example in the U.S. Pharmacopeia.

The suitability of particular carriers for inclusion in a given therapeutic composition depends on the preferred route of administration. For example, antifungal compositions may be formulated for oral administration. Such compositions are typically prepared as liquid solution or suspensions or in solid forms. Oral formulation usually include such additives as binders, fillers, carriers, preservatives, stabilizing agents, emulsifiers, buffers, mannitol, lactose, starch, magnesium stearate, sodium saccharin, cellulose, magnesium carbonate, and the like. These compositions may take the form of solutions, suspensions, tablets, pills, capsules, sustained release formulations, or powders, and typically contain 1% to 95% of active ingredient. More preferably, the composition contains from about 2% to about 70% active ingredient.

Compositions of the present invention may be prepared as injectables, either as liquid solutions, suspensions, or emulsions; solid forms suitable for solution in or suspension in liquid prior to injection. Such injectables may be administered subcutaneously, intravenously, intraperitoneally, intramuscularly, intrathecally, or intrapleurally. The active ingredient or ingredients are often mixed with diluents, carriers, or excipients which are physiologically tolerable and compatible with the active ingredient(s). Suitable diluents and excipients are for example, water, saline, dextrose, glycerol, or the like and combinations thereof. In addition, if desired, the compositions may contain minor amounts of auxilary substances such as wetting or emulsifying agents, stabilizing or pH buffering agents.

For use in controlling a fungal infection, a cream, foam, or ointment may be especially preferred.

The effectiveness of the claimed compounds can be assessed using standard methods known to the skilled artisan. Examples of such methods are as follows:

1. Disk Diffusion Assay.

Activity of the Compounds of Formula I and Formula II can be illustrated with representative assay results in a disk diffusion assay. Filamentous fungi used in the assays are prepared from stock cultures which have been maintained on potato dextrose agar and transferred serially at two week intervals using standard microbiological techniques. Yeast used are prepared from stock cultures of strains of yeast which have-been maintained frozen at −80° C. in 20% aqueous glycerol.

Seeded agar assay plates are prepared according to the type of assay strain. Inoculum for filamentous fungi is prepared by scraping the surface of stock plates with a moistened sterile dacron swab. The spores and mycelia are then suspended in 10 milliliters of sterile potato dextrose broth and adjusted to 70% transmittance at 660 nm. Inoculum for Cryptococcus is prepared from overnight broth cultures. Cultures are then diluted into potato dextrose broth to a final concentration of either 40% or 70% transmittance at 660 nm. Assay plates are prepared by diluting the inoculum into appropriate molten agar medium, and thereafter cooling to about 45° C., to yield a final concentration of four percent.

Samples are applied to 6.2 mm filter paper disks and air dried at about 24° C. The disks are then applied to seed assay plates with sterile forceps and rewetted with sterile 25 percent aqueous dimethyl sulfoxide. The assay plates are then incubated for about 24 hours.

Following incubation, inhibition zones are measured and recorded. Measurements are made from the extreme edge of a zone where the growth differed from the background. Inhibition zones are further qualified as fuzzy, a zone that had a fuzzy edge and clear center surrounding the disk; hazy-a zone that was hazy throughout; slightly hazy-a zone in which low levels of growth are discernible throughout the inhibition zone; and very hazy-a zone in which the differences between background and inhibition zone are barely discernible. Zones without a qualifier are those which were clear throughout.

Mycotic Assay.

The mycotic activity of the compounds can be illustrated with test results against *Cryptococcus neoformans* employing yeast nitrogen based dextrose agar medium. The test compound is solubilized in 10 percent dimethyl sulfoxide supplemented with one drop of Tween 20. Twofold dilutions are made with sterile distilled water/10 percent dimethyl sulfoxide to obtain final drug concentrations in the agar dilution assay plates ranging from 128 to about 0.06 ug/ml against two strains of against *Cryptococcus neoformans* and subsequently against an expanded panel of over 75 other strains at concentrations ranging from 0.008 to 16 ug/ml.

Nystatin or amphotericin B are used as a positive control.

Mdr-inhibitor

A clinical isolate of *Aspergillus fumigatus*, strain 10 AF (Eli Lilly and Company) is used in antifungal susceptibility/potentiation tests. Spores of *A. fumigatus* strain 10AF are prepared by inoculating Potato dextrose agar with spores from long term storage. These plates are incubated with 35° C. for 24 hours and then an additional one to two days at room temperature until sporulation is evident. Spores are harvested by flooding the plate with 0.05% Tween 80 solution and gently scraping the surface of the plate to suspend the spores. Spores are harvested by centrifugation and resuspended in a cold storage preservation medium containing 50 g/L lactose, 100 ml/L glycerol, and 850 ml water. Spore suspensions prepared in this manner remain viable for several months when stored at −70° C.

Approximately $1\times10^6$/ml *Aspergillus fumigatus*, strain 10 AF (Eli Lilly and Company) spores are suspended in autoclaved Trypticase Soy agar (cooled) and 15 ml of suspension and delivered to each of several petri plates. The agar surfaces of the plates are allowed to dry.

The antifungal compound R106I is dissolved in 100% ethanol at a concentration of either 1 or 7 mg/ml. The antifungal compound R106I is disclosed in U.S. Pat. No. 5,057,493, which is hereby incorporated herein by reference. Twenty ul of the 1 mg/ml test compound solution is delivered to an antibiotic susceptibility test disk. After addition of the antibiotic solution the discs are allowed to dry. When dry the discs are placed on the surface of the petri plates containing *Aspergillus fumigatus*, strain 10 AF spores.

Compounds to be tested for the potentiation of the antifungal activity of R106I (i.e. putative potentiating agent) against *Aspergillus fumigatus*, strain 10 AF are dissolved in dimethylsulfoxide. The amount of compound added to the dimethylsulfoxide depends on the solubility of the individual test compound. Twenty ul of the suspensions containing the compounds to be tested are delivered to an antibiotic susceptibility test disc. The discs containing the test compounds are allowed to air dry. These discs are then placed on the surface of the dried petri plates containing the *Aspergillus fumigatus*, strain 10 AF spores approximately 2 cm from the antifungal containing disc. Petri plates containing the two discs are incubated overnight. The next day the plates are examined for zones of growth inhibition around the zones.

Compounds of this invention can be prepared using the following methods:

Compounds of Formula IA can be prepared as follows:

IA

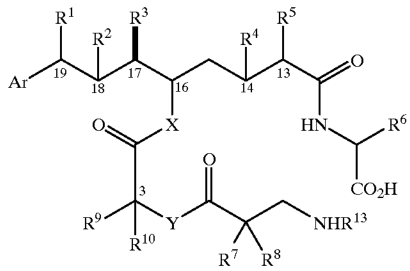

Wherein

Ar is phenyl or any simple unsubstituted or substituted aromatic or heteroaromatic group;

$R^1$ is halogen, SH, amino, monoalkylamin.o, dialkylamino, trialkylammonium, alkylthio, dialkylsulfonium, sulfate, or phosphate;

$R^2$ is OH or SH; or $R^1$ and $R^2$ may be taken together to form an epoxide ring, and aziridine ring, an episulfide ring, a sulfate ring, or monoalkylphosphate ring; or $R^1$ and $R^2$ may be taken together to form a second bond between $C_{18}$ and $C_{19}$;

$R^3$ is a lower alkyl group;

$R^4$ is H;

$R^5$ is H;

$R^4$ and $R^5$ may be taken together to form a second bond between $C_{13}$ and $C_{14}$;

$R^6$ is benzyl, hydroxybenzyl, alkoxybenzyl, halohydroxybenzyl, dihalohydroxybenzyl, haloalkoxybenzyl, or dihaloalkoxybenzyl group, a substituent selected from the group consisting of B-ring heteroaromatic, substituted heteroaromatic, B-ring ($C_1$–$C_6$)alkyl, ($C_3$–$C_8$)cycloalkyl, substituted $C_3$–$C_8$ cycloalkyl, substituted ($C_1$–$C_6$)alkyl, and a group of the formula III':

III'

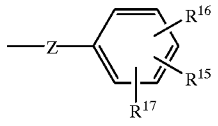

;

$R^7$ is H or a lower alkyl group;

$R^8$ is H or a lower alkyl group;

$R^9$ is H or a lower alkyl group;

$R^{10}$ is H or a lower alkyl group;

$R^{13}$ is selected from the group consisting of di-tert-butyl dicaronate and tert-butyl dicarbonate;

$R^{15}$, $R^{16}$, and $R^{17}$ are each independently selected from the group consisting of hydrogen, $OR^{18}$, halo, $NH_2$, $NO_2$, $OPO_4H_2$, $OR^{19}$phenyl, and ZZ;

$R^{18}$ is $C_1$–$C_6$ alkyl;

$R^{19}$ is $C_1$–$C_6$ alkyl;

n is 0, 1, or 2;

X is O, NH or alkylamino;

Y is C, O, NH, S, SO, $SO_2$ or alkylamino;

Z is selected from the group consisting of $—(CH_2)_n—$ and ($C_3$–$C_5$)cycloalkyl;

comprising contacting a compound of the formula:

IVA

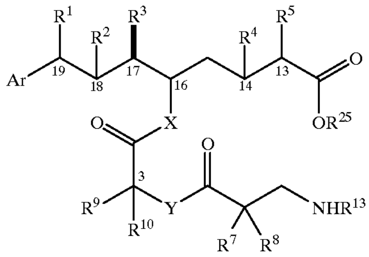

$R^{25}$ is an active ester substituent;

with an acid of the formula:

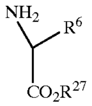

;

$R^{27}$ is a an acid/weak base active ester substituent;

and a silylating agent in the presence of a solvent.

As used with regard to $R^{25}$ the phrase "active ester substituent" refers to a substituent which makes the $OR^{24}$ substituent a good leaving group. Appropriate substituents can be selected with guidance from standard reference guides, for example, "Protective Groups in Organic Chemistry", Plenum Press, (London and New York, 1973); Greene, T. W. "Protecting Groups in Organic Synthesis", Wiley (New York, 1981). Especially preferred $R^{25}$ groups are selected from di-tert-butyl dicaronate and tert-butyl dicarbonate(BSA). BSA is especially preferred.

The artisan can select an appropriate solvent for the above described process. Inert organic solvents are particularly preferred; however, under certain conditions an aqueous solvent can be appropriate. For example, if $R^{27}$ is hydrogen and and $R^{13}$ is BSA an aqueous solvent will be effective.

When the desired $R^6$ substituent in the compound of Formula I contains an amine, then the amine substituent of the $R^6$ group must be protected using an amino protecting group. The artisan can readily select an appropriate amino protecting group using guidance from standard works, including, for example, "Protective Groups in Organic Chemistry", Plenum Press, (London and New York, 1973); Greene, T. W. "Protecting Groups in Organic Synthesis", Wiley (New York, 1981).

$R^{27}$ is a an "acid/weak base active ester substituent" wherein this phrase means that the $R^{27}$ substituent forms an active ester substituent when attached to the $—CO_2$ group provided that the $—CO_2R^{27}$ substituent can be removed using acidic, neutral, or mild basic conditions. Preferred $R^{27}$ groups include, but are in no way limited to, hydrogen, C—C alkyl, tricholoromethyl, trichloroethyl, and BSA. It is especially preferred that R27 is hydrogen.

Generally known silylating agents are employed. See for example, Calvin, E. W., "Silicon Reagents in Organic Synthesis", Academic Press, (London, 1988). Particularly useful silylating agents include "tri-lower alkyl silyl" agents, the term of which contemplates triusopropylsilyl, trimethylsilyl and triethylsilyl, trimethylsilyl halides, silylated ureas such as bis(trimethylsilyl)urea (BSU) and silylated amides such as N,O-bis(trimethylsilyl)acetamide (BSA). Of these, BSA is preferred.

Suitable inert organic solvents include those known to the skilled artisan, for example, but not limited to, tetrahydrofuran (THF) and dimethylformamide (DMF). DMF is especially preferred.

Some preferred characteristics of this invention are set forth in the following tabular form wherein the features may be independently selected to provide preferred embodiments of this invention. The invention is in no way limited to the features described below:

A) $R^8$ is ethyl, propyl, isopropyl, butyl, isobutyl or isopentyl;

B) $R^7$ is ethyl, propyl, isopropyl, butyl, isobutyl, pentyl, or isopentyl;

C) $R^7$ is H, $R^8$ is methyl, $R^3$ is methyl, and X and Y are not both O;

D) $R^3$ is ethyl, propyl, isopropyl, butyl, isobutyl, pentyl or isopentyl;

E) $R^9$ is methyl, ethyl, propyl, butyl, isobutyl, pentyl, or isopentyl;

F) $R^{10}$ is methyl, ethyl, propyl, butyl, isobutyl, pentyl, or isopentyl;

G) a cryptophycin compound wherein at least one of the groups selected from the group consisting of C-3, C-6, C-7, C-10, C-16, C-17, and C-18 has R stereochemistry (numbering as set forth in claim 1 infra.);

H) a cryptophycin compound wherein at least one of the groups selected from the group consisting of C-3, C-6, C-7, C-10, C-16, C-17, and C-18 has S stereochemistry (numbering as set forth in claim 1 infra.);

I) Ar is phenyl with a substituent selected from the group consisting of hydrogen, halogen, and simple alkyl;

J) a compound wherein Y is selected from the group consisting of O, NH, S, SO and $SO_2$;

K) a compound wherein Y is C, $R^7$, $R^8$, $R^9$, and $R^{10}$ are each hydrogen; and $R^1$ and $R^2$ form an epoxide;

L) $R^7$, $R^8$ are each hydrogen;

M) $R^7$ and $R^8$ are each selected from hydrogen or OH;

N) Y is O;

O) R is selected from the group consisting of methyl, ethyl, n-propyl, and phenyl;

P) $R^1$ and $R^2$ form an epoxide ring; Q) both X and Y are O;

R) $R^4$ and $R^5$ form a double bond;

S) $R^6$ is substituted benzyl wherein one substituent is a halogen and one is an $OR^{12}$ group wherein $R^{12}$ is lower alkyl;

T) Y is O or S; and

U) Y is selected from S, SO, and $SO_2$;

V) the process for preparing a compound of formula IVA is completed in the presence of an inert organic solvent or mixture of inert organic solvents;

W) Formula I compound is used to control a fungal infection;

X) Formula II compound is used to control a fungal infection;

Y) Formula I is used to control a mycotic infection;

Z) Formula II is used to control a mycotic infection;

AA) Formula I is used to control a yeast infection;

BB) Formula II is used to control a yeast infection;

CC) Formula I is used to control a parasite infection;

DD) Formula II is used to control a parasite infection; and

EE) Formula IA is used to provide mdr inhibitor activity.

To provide further guidance for the artisan, the following schemes are provided:

SCHEME I

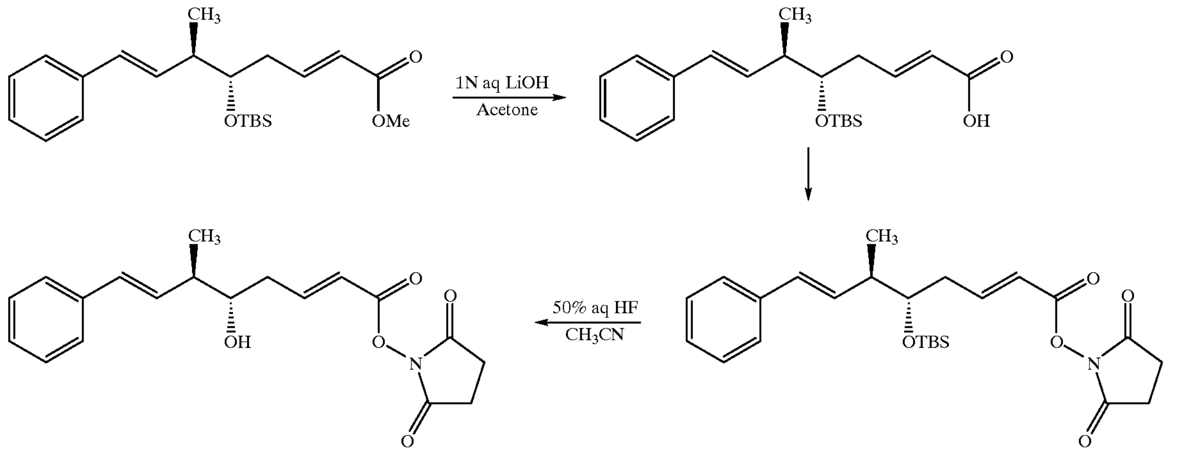

SCHEME I'

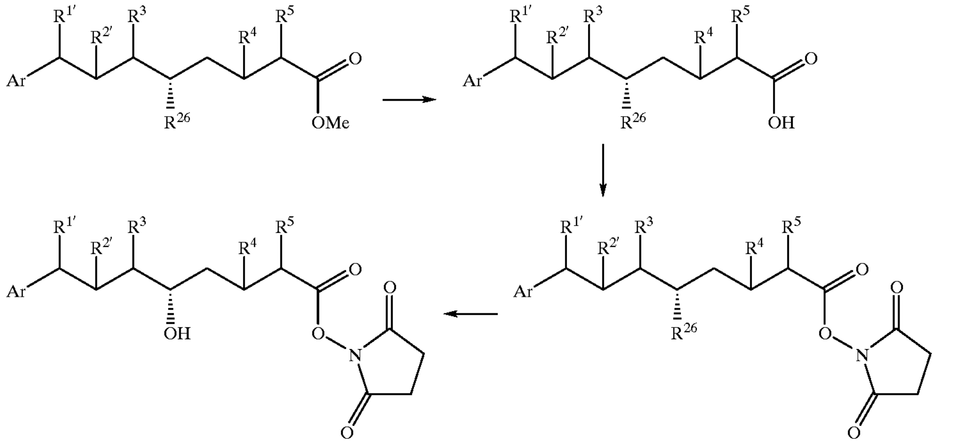

As used in Scheme I' and throughout the specification, $R^{1'}$ is halogen, SH, amino, monoalkylamino, dialkylamino, trialkylammonium, alkylthio, dialkylsulfonium, sulfate, or phosphate; $R^2$ is OH or SH; $R^{26}$ is an alcohol protecting group introduced during a portion of the synthetic process to protect an alcohol group which might otherwise react in the course of chemical manipulations, and is then removed at a later stage of the synthesis. Numerous reactions for the formation and removal of such a protecting group are described in a number of standard works, including, for example, "Protective Groups in Organic Chemistry", Plenum Press, (London and New York, 1973); Greene, T. W. "Protecting Groups in Organic Synthesis", Wiley (New York, 1981). The skilled artisan can select an appropriate alcohol protecting group particularly with guidance provided from such works. One particularly useful alcohol protecting group is tert-butyldimethylsilyl (TBS).

Scheme 2

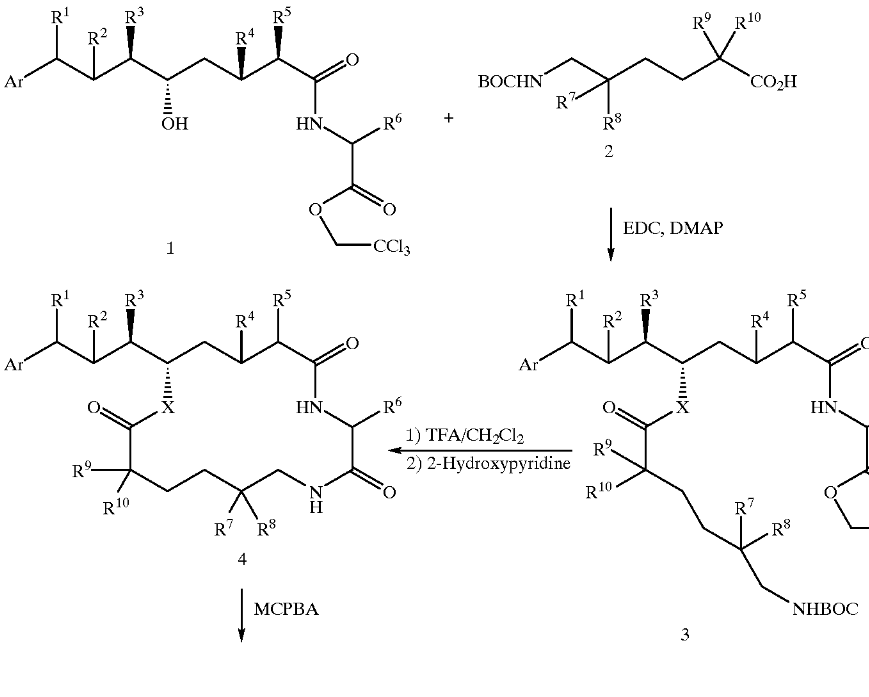

-continued

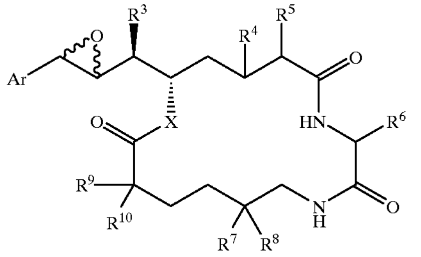

5

Particular compounds claimed herein can be prepared using the scheme 2A provided below as an example for the convenience of the artisan.

Scheme 2A

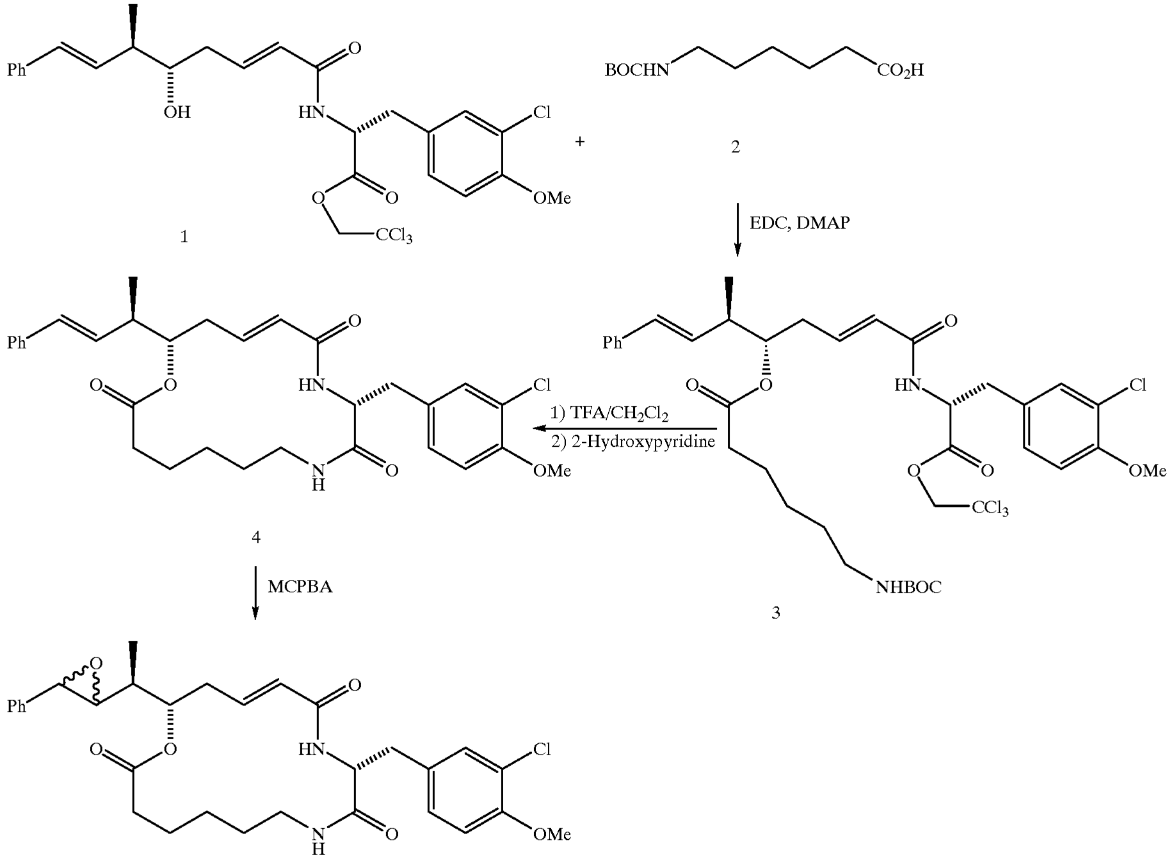

1 2 3 4 5

The artisan can utilize appropriate starting materials and reagents to prepare desired compounds using the guidance of the previous schemes and following examples.

The necessary reaction time is related to the starting materials and operating temperature. The optimum reaction time for a given process is, as always, a compromise which is determined by considering the competing goals of throughput, which is favored by short reaction times, and maximum yield, which is favored by long reaction times.

To further illustrate the invention the following examples are provided. The scope of the invention is in no way to be construed as limited to or by the following examples.

Preparation 1

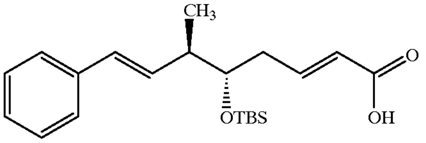

Methyl ester (2.673 mmol) was dissolved in acetone and then 1N aqueous LiOH (26 mL) added at room temperature. The cloudy mixture was further diluted with acetone (20 mL) and the resulting yellow mixture stirred at room temperature for 23.5 h. The reaction was diluted with diethylether (400 mL) and the organics washed with 1N HCl (120 mL), brine (200 mL) and $H_2O$ (160 mL). The organics were dried and concentrated in vacuo to leave a yellow oil which was purified by column chromatography (gradient: 5% AcOH+20%–40% EtOAc/Hexanes to give carboxylic acid as a yellow oil (960 mg, 100%).

$^1$H NMR ($CDCl_3$) d 7.38–7.19 (m,PhH5), 7.09 (ddd,J=15.2, 7.6 and 7.9 Hz,3—H), 6.38 (d,J=16 Hz,8—H), 6.16 (dd,J=16 and8 Hz, 7—H), 5.85 (d,J=15.8 Hz,2—H), 3.81–3.75 (m,5—H), 2.49–2.37 (m,6—H,4—$CH_2$), 1.12 (d,J=6.7 Hz,6—Me), 0.91 (s,$SiCMe_3$), 0.065 (s,SiMe), 0.068 (s,SiMe) ppm;

IR u ($CHCl_3$) 2957,2930,2858,1697,1258,1098,838 $cm^{-1}$;

MS (FD) 360.2 ($M^+$,100);

$[a]_D$+87.6° (c 10.5, $CHCl_3$);

Anal. calcd. for $C_{21}H_{32}O_3$ requires: C,69.95; H,8.95%. Found: C,69.19; H,8.39%.

Preparation 2

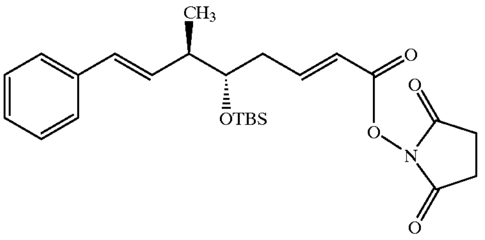

To a stirred solution of carboxylic acid (2 mmol) in dry dimethylformamide (5.5OmL) was added 1-ethyl-3-(3-dimethyaminopropyl)carbodiimide (2.4 mmol) and N-hydroxysuccinimide (2.6 mmol) at room temperature. The mixture was stirred for 28 h and then diluted with EtOAc (lOOmL) and washed with 1N aqueous HCl (2×50 mL), $H_2O$ (75 mL), dried and concentrated in vacuo to leave an oil. Crude product was purified by column chromatography (gradient: 5–30% EtOAc/Hexanes) to give active ester as a pale yellow oil (724mg,80%).

$^1$H NMR ($CDCl_3$) d 7.36–7.20 (m,$PhH_5$,3—H), 6.38 (d,J=16 Hz,8-H), 6.14 (dd,J=16.1 and 8.0 Hz,7—H). 6.03 (d,J=16 Hz,2—H), 3.79 (q,J=4.3 Hz,5—H), 2.94 (brs, $CH_2CH_2$), 2.58–2.42 (m,6—H,4 —$CH_2$), 1.10 (d,J=6.8 Hz,6—Me), 0.90 (s,$SiCMe_3$), 0.05 (s,$SiMe_2$) ppm;

IR u ($CHCl_3$) 2957,2931,2858,1772,1741,1648,1364,1254,1092,1069,838 $cm^{-1}$;

MS (FD) 457 ($M^+$,100);

$[a]_D$+71.30 (c 10.1, $CHCl_3$);

Anal. calcd. for $C_{25}H_{35}NO_5$ requires: C,65.61;H,7.71;N, 3.06%. Found: C,65.51;H,7.56; N, 3.02%.

Preparation 3

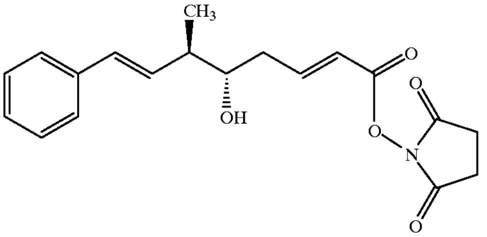

To a stirred solution of silyl ether (2.50g,5.47 mmol) in $CH_3CN$ (130 mL) was added 48% aqueous HF (15 mL) at 0° C. The solution was stirred at 0° C. for 0.75 h and then at room temperature for 4 h. The reaction was diluted with diethylether (300 mL) and washed with $H_2O$ until the wash ws~pH7. Organics were dried ($MgSO_4$) and concentrated in vacuo to give a yellow residue which was recrystallized from Et2O to give alcohol as white crystals (1.46g,78%).

$^1$H NMR ($CDCl_3$) d 7.41–7.20 (m,$PhH_5$,3—H), 6.48 (d,J=16 Hz,8—H), 6.15–6.07 (m,7—H,2—H), 3.71–3.65 (m,5—H), 2.83 (brs,$CH_2CH_2$), 2.60–2.33 (m,6—H,4—$CH_2$),1.95 (brs, 5—OH), 1.14 (d,J=6.8 Hz,6—Me) ppm;

IR u (KBr) 3457,1804,1773,1735,1724,1209,1099,1067,1049,975,744, 694 $cm^{-1}$;

UV (EtOH) $l_{max}$ 250 (e=20535) nm;

MS (FD) 343.2 ($M^+$,100);

$[a]_D$ -57.80 (c 10.56, $CHCl_3$);

Anal. calcd. for $C_{19}H_{21}NO_5S$ requires: C,66.46;H,6.16;N,4.08%. Found: C,66.49; H,6.16; N, 4.07%.

Preparation 4

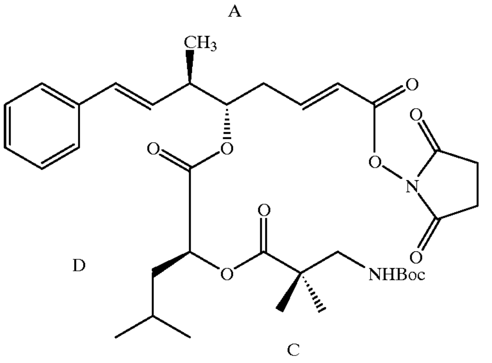

To a suspension of carboxylic acid (1.28g, 3.87 mmol), in dry dichloromethane (6 mL) was added EDC (742 mg,3.87 mmol) and DMAP (73 mg,0.60 mmol) and the mixture stirred at room temperature for 0.5 h. A solution of alcohol (1.02 g, 2.97 mmol) in dichlormethane (5.5 mL) was added to the reaction mixture and stirred for a further 0.3 h. The reaction was diluted with $CH_2Cl_2$ (200 mL) and washed with 1N aq. HCl (2×50 mL), sat. aq. $NaHCO_3$ (2×50 mL), $H_2O$ (50 mL). The organics were dried ($MgSO_4$) and concentrated in vacuo to leave an oily residue, which was purified by column chromatography (gradient: 10–30% EtOAc/Hexanes) to give the desired ester as a yellow solid (1.68 g,79%).

$^1$H NMR ($CDCl_3$) unit A d 7.35–7.20 (m,$PhH_5$,3—H), 6.43 (d,J=15.8 Hz,8—H), 6.12 (d,J=15.9 Hz,2H), 5.99 (dd,J=

8.5 and 15.8 Hz,7—H), 5.06–5.08 (m,5—H), 2.85 (brs, $CH_2CH_2$), 2.68–2.61 (m,6—H,4—$CH_2$), 1.13 (d,J=6.8 Hz,6—Me); unit C d 5.31 (brt,NH),3.28–3.25 (m,3—$CH_2$),1.43 (s,$CMe_3$), 1.21 (s,2—Me), 1.19 (s,2—Me); unit D d 4.95 (dd,J=9.8 and 3.8 Hz,2—H), 1.73–1.64 (m,3—H,4—H), 1.59–1.49 (m,3—H'), 0.85 (d,J=6.4 Hz,5—Me), 0.82 (d,J=6.4,4—Me) ppm;

IR u (KBr) 3400, 2975,1743,1367,1206,1126,1145,1068 $cm^{-1}$;

MS (FD) 657 ($M^+$,100);

$[a]_D$+39.5° (c 10.38, $CHCl_3$);

Anal. calcd. for $C_{35}H_{48}N_2O_{10}$ requires:

C,64.01;H,7.37;N,4.27%. Found: C,64.19;H,7.27; N,4.52%.

Preparation 5

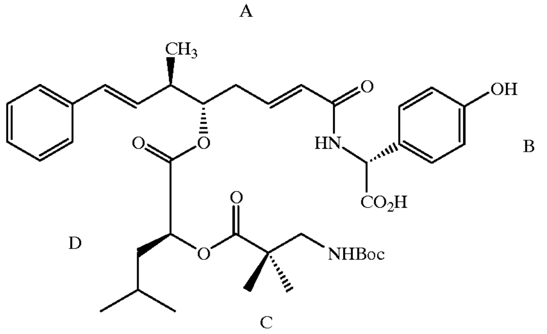

To a stirred solution of active ester (150 mg, 0.229 mmol) in dry DMF (2.5 mL) was added N,O-Bis-(trimethylsilyl) acetamide (282 uL,1.143 mmol) followed by D-Hydroxy-phenylglycine (57 mg,0.343 mmmol). The mixture was heated in a sealed tube under $N_2$ at 55° C. for 20 h. Reaction solution was diluted with EtOAc (180 mL) and washed with 1N aq. HCl (50 mL),$H_2O$ (50 mL), brine (50 mL), dried (MgSO4) and concentrated in vacuo to give a yellow solid. Purification of the crude solid by column chromatography (gradient: 5–20% MeOH/$CH_2Cl_2$) provided amide (122 mg,75%).

$^1$H NMR ($CD_3OD/CDCl_3$) Unit A d 7.27–7.20 (m,PhHs), 6.75–6.69 (m,3—H), 6.43 (d,J=15.9 Hz,8—H), 5.96 (d,J=15.7 Hz,7—H), 5.93 (d,J=15.6 Hz,2—H), 4.95–4.93 (m,5—H), 2.56–2.49 (m,6—H,4—$CH_2$), 1.04 (d,J=6.8 Hz,6—Me); Unit B d 7.16 (d,J=8.3 Hz,$ArH_2$), 6.66 (d,J=8.2 Hz,$ArH_2$), 5.62 (brt,NH)5.19–5.18 (m,2—H); Unit C d 3.15 (d, J=6.3 Hz,3—$CH_2$), 1.36 (s,$CMe_3$), 1.11 (s,2—Me), 1.08 (s,2—Me); Unit D d 4.85 (dd,J=9.6 and 3.3 Hz,2—H), 1.64–1.57 (m,3—H,4—H), 1.55–1.47 (m,3—H'), 0.76 (d, J=6.3 Hz,5—Me), 0.73(d,J=6.3 Hz,4—Me) ppm;

IR u (KBr) 3400,2972,1728,1672,1614,1515,1450,1416, 1171,1147 $cm^{-1}$;

MS (FAB) 610.6 ($[MH_2\text{-Boc}]^+$,100);

$[a]_D$ -19.90 (c 6.53, MeOH).

Preparation 6

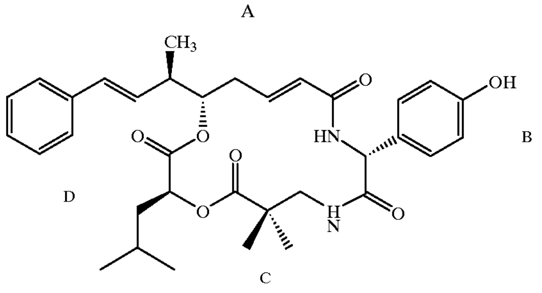

Boc amine as prepared by Preparation 5 (109mg,0.154 mmol) was dissolved in trfluoracetic acid (5 mL,5 mM) and stirred at room temperature for 2 h. The reaction was concentrated in vacuo and dried under high vacuum to give the trifluoroacetate salt of amine as a light brown foam. Crude amine salt (max. 0.154 mmol) was dissolved in dry DMF (31 mL) and diisopropylethylamine (80 uL,0.462 mmol), followed by pentafluorophenyl diphenyl -phosphinate (77mg,0.2 mmol) added. The resulting solution was stirred at room temperature under dry $N_2$ for 15 h, concentrated in vacuo and the residue purified by column chromatography (gradient: 1–4% MeOH/$CH_2Cl_2$) to provide cryptophycin as a tan solid (54 mg,59%).

$^1$H NMR ($CDCL_3$) Unit A d 7.36–7.15 (m,PhHs), 6.79–6.69 (m,3-H), 6.54 (d,J=15.8,8—H), 5.98 (dd,J=15.8 and 8.8 Hz,7—H), 5.06–5.0 (m,5—H), 2.61–2.49 (m,6—H,4—H), 2.39–2.30 (m,3—H'), 1.10 (d,J=6.8 Hz,6—Me); Unit B d 7.90 (dd,J=10 and 1.68 Hz,OH), 7.65 (d,J=6.3 Hz,NH), 7.10 (d,J=8.5,$ArH_2$), 6.71 (d,J=8.4,$ArH_2$), 5.28 (d,J=6.5 Hz,2—H), ; Unit C d 3.55–3.47 (dd,J=13.3 and 10.1 Hz,3—$CH_2$), 3.00 (d,J=13.4 Hz,NH) 1.19 (s,2—Me), 1.16 (s,2—Me); Unit D d 4.90 (dd,J=10 and 3.5 Hz,2—H), 1.66–1.54 (m,3—H,4—H), 1.32–1.25 (m,3—H'), 0.67 (apparent t,J=7.1 Hz,5—Me,4—Me) ppm;

IR u (KBr) 3418,3340,2960,1740,1713,16711514,1271,1198,1155,972 $cm^{-1}$;

MS (FD) 590 ($M^+$,100);

$[a]_D$+15.35° (c 3.91, $CHCl_3$).

Preparation 7

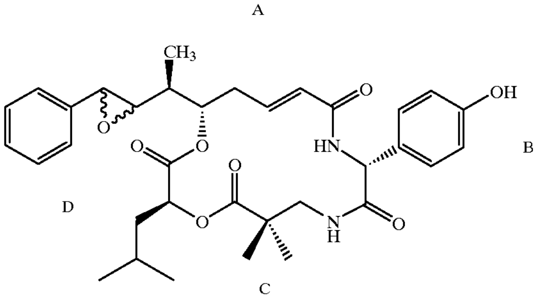

Styrene prepared as described by Example 3 (42 mg, 0.0712 mmol) was suspended in dry dichloromethane (2.2 mL, 0.035mM) and mCPBA(49 mg, 0.285 mmol) added in one portion at room temperature. Dry tetrahydrofuran (0.3 mL) was added to produce a homogeneous solution. The reaction was stirred under $N_2$ at room temperture for 21 h and then diluted with further $CH_2Cl_2$ (15 mL). Organics were washed with 10% aq. $Na_2S_2O_5$ (10 mL), sat. aq. $NaHCO_3$ (10 mL), $H_2O$ (10 mL), dried ($MgSO_4$) and concentrated in vacuo to give a yellow solid. Crude product was initially purified by column chromatography (gradient: 1–5% $MeOH/CH_2Cl_2$) to give a 1: 1.15 mixture of a:b $C_7$–$C_8$ epoxides as a white solid (23 mg, 54%).Reverse phase HPLC (column: 4.6×250 mm Kromsil C18;

Eluent: 60% $CH_3CN/H_2O$; Flow: 1.0 mL/min; UV: 220 nm) separation of the a:b mixture provided a-epoxide (2.3 mg, t=13.7 min) and b-epoxide (5.8 mg, t=12.1 min) as white solids.

EXAMPLE 1

Cryptophycin 52 ("Compound I")

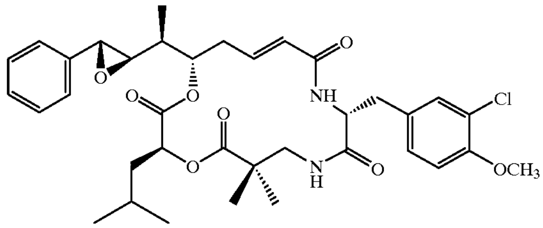

A racemic trans-3-penten-2-ol (933 mg), trifluoroethyl laurate (4.14 g) and porcine pancreatic lipase (PPL, 2.0 g) in about 25 ml of anhydrous diethyl ether was stirred for 80 hours. The PPL was then filtered off and washed with ether. The ether filtrate was evaporated and the sticky oil was then subjected to short-path vacuum distillation. The S-trans-3-penten-2-ol (A) was condensed in a liquid nitrogen cooled trap (383 mg) and identified using NMR.

The material was then vigorously stirred with tetrabutylammonium hydrogen sulfate and 40% NaOH in water at 0 C. Propargyl chloride was added dropwise to the mixture (767 mg). Vigorous stirring was continued overnight after which time the mixture was neutralized with HCL at 0 C and the propargyl ether extracted into pentane. The extract was evaporated and the propargyl ether was purified on a short silica column to give propargyl ether B which was characterized using NMR, An aliquot of butyl lithium hexane solution (2.5 M, 5.1 ml) was evaporated in vacuo and the residue cooled to −90° C. A solution of propargyl ether B (454 mg) in 10 ml of tetrahydrofuran was slowly added. After allowing the temperature to increase to room temperature overnight, the reaction mixture was quenched with $NH_4Cl$ solution. Extraction with ether evaporation and purification of the residue gave 322 mg of alcohol C which was characterized by NMR.

To a stirred solution of alcohol C (248 mg) and imidazole (340 mg) in 3 mL of dry DMF was added tert-butyldimethylsilyl chloride (452 mg). After stirring the mixture overnight, 10 mL of NaOH was added to destroy the excess ter-butyldimethylsilyl chloride. The product was extracted into ether and the extract washed, dried and evaporated. Purification of the residue by chromatography on silica gel with hexane gave 457 mg of (3R,4R)-3-tert-butyldimethylsilyloxy-4-methylhept-5-(E)-en-1-yne (D) (96% yield) and was characterized by NMR.

2-methylbutene (1.15 mL 2M folution in THF) was added to 1.1 mL of $BH_3$ THF solution 1M at −25 C and the mixture was stirred in an ice bath for two hours. The temperature was then cooled to −50 C and a solution of the TBS derivative (238 mg) in 1 ml of THE was added all at once. The cooling bath was removed and the reaction mixture was allowed to warm to and to remain at room temperature for 1 hour. Then 2.2 M. $KH_2PO_4/K_2HPO_4$ solution (4.8 mL) and 30% $H_2O_2$ (0.8 mL) were added at 0 C. One hour later, the THF was evaporated and the residue extracted into ether. The dried ether extract was evaporated and the residue chromatographed on silica gel to give 194 mg of aldehyde D, which was characterized by NMR.

To a stirred solution of aldehyde D (0.74 g) and trimethyl phosphonoacetate (632 mg) in 5 mL of THF cooled to −78 C was added tetramethylguanidine (435 uL). After 30 minutes the cooling bath was removed and the mixture was stirred for another four hours. The mixture was neutralized with 1 N HCl and the product was extracted into ether. Evaporation of the dried ether extract left a residue which was chromatographed on silica gel to give 0.814 g of E (90% yield) and was characterized by NMR.

Ozone was passed through a solution of methyl ester E (328 mg) and 97 uL of pyridine in 15 mL of $CH_2Cl_2$ at −78 C and the progress of the ozonolysis was monitored by TLC analysis. After the methyl ester had been consumed, about 500 mg of zinc dust and 1 mL of glacial acetic acid were added. The temperature was slowly increased to 25 C. The mixture was filtered and the filtrate was washed successively with saturated $CuSO_4$ and $NaHCO_3$ solutions. After evaporation of the solvent, the crude aldehyde F (249 mg) in the next step without purification.

To a stirred solution of aldehyde F (25.0 mg), in 1.5 mL of THF at −78 C was added 0.80 mL of a cold (−78 C) mixture of benzyltriphenylphosphonium chloride (268 mg) and n-butyl lithium (280 uL in hexane). After 15 minutes, the cold bath was removed and the stirring was continued for 2 hours. The reaction was quenched with saturated ammonium chloride solution and the THF was evaporated. The concentrate was extracted with hexane and the combined extract was washed with brine, dried, and evaporated. The residual oil was dissolved in 1.5 mL of benzene containing thiophenol (0.02 M) and 1,1' azobis (cyclohexanecarbonitrile) and the mixture was refluxed for 5 hours. After cooling to room temperature, hexane (15 mL) was added and the organic solution was washed successively with 10% NaOH and brine, dried and evaporated. Chromatography of the residue on silica gel let to 24 mg of G.

To a solution of ester G (159 mg) in 7 mL of acetone was added 5 mL of 1N LiOH. The mixture was stirred at 25 C for 3 hours, diluted and acidified to about pH 4 with 1N HCl. The organic layer was separated and washed, dried, and evaporated. Chromatography of the residual oil on silica gel with 40% EtOAc in hexane containing 0.5% AcOH resulted in pure acid H as a pale yellow mobile oil (145 mg).

A sample of the D-chlorotyrosine BOC derivative (160 mg) was dissolved in 3 mL neat trifluoroacetic acid and allowed to stand at room temperature for one hour. Removal of the excess reagent under reduced pressure returned the desired amine I as the trifluoroacetate salt(I).

To a stirred solution of acid H (25 mg) in 3 mL of anhydrous DMF under argon was added successively pentafluorodiphenylphosphinate (FDPP, 32 mg), trifluoroacetate salt I (35 mg) and diisopropylethylamine (DIEA, 27 mg). Stirring was continued at 25 C for 1 hour and the reaction mixture was extracted. The ether extract was washed, dried, and evaporated. The residual pale yellow oil was subjected to chromatography on silica gel (15% in hexane) to give J as a colorless oil (32 mg). J was characterized by NMR.

To a solution of J (50 mg) in 4 mL MeCN was added 400 mL of 49% aq HF and the mixture stirred for 1 hour at 25 C. Extraction followed by washing the ether extract, drying and evaporation gave alcohol K as a colorless foam (40 mg)

To a solution of 3-amino-2,2-dimethylpropan-1-ol (L) (3.0g) in 51 mL of a 10% solution of triethylamine in MeOH was added di-tert-butyl dicarbonate (6.7 g) and the mixture was stirred for 1 hour at 25 C. After removal of the solvent, the residue was dissolved in $CH_2Cl_2$ and the solution was washed and dried. Removal of solvent in vacuo afforded 5.8 g of 3-(tert-butoxycarbonyl)amino-2,2-dimethylpropan-1-ol as a white solid which was directly used for the next step without further purification.

To a solution of alcohol 3-(tert-butoxycarbonyl)amino-2,2-dimethylpropan-1-ol (5.3 g) and sodium periodate (16.6 g) in carbon tetrachloride, acetonitrile and water was added ruthenium trichloride hydrate (122 mg) and the mixture was stirred at 25 C for 1 hour. The mixture was filtered through celite and a saturated solution of potassium carbonate in water was added. The water layer was separated, washed with ether, acidified to pH 2 at 0 C and extracted. The combined extracts were washed with saturated NaCl solution and dried. Removal of solvent in vacuo yielded a residue that was first subjected to flash reverse phase chromatography on a C18 silica and then crystallized from ether to give 3.7 g of M as a white solid. M was characterized by NMR.

To a solution of 2.66 gram of L-leucic acid (20 mmol) and 1.74 gram of sodium bicarbonate (20 mmol) in 30 mL water at 0 C was added a soltion of 6.44 g tetrabutylammonium chloride (20 mmol) and 1.74 mL of allyl bromide (20 mmol). After vigorously stirring the mixture for 24 hours the solvent was evaporated. The residue was passed through a short silica column to give 3.21 g of allyl ester N as a colorless oil.

To a solution of 0.8 g of M (3.7 mmol), 0.76 g of N (4.4 mmol) and 92 mg DMAP in 10 mL of dry $CH_2Cl_2$ at 0 C was added 0.84 g of DCC (4.1 mmol) in $CH_2Cl_2$. The mixture was stirred at 25 C for 3 hours and filtered. The filtrate was washed with saturated aqueous sodium bicarbonate, dried and evaporated in vacuo. Flash chromatography afforded 1.0 g of pure 0 as a colorless oil.

To a 10 mL solution of 180 mg of 0 and 60 mg of tetrakis (triphenylphosphine)palladium in dry THF was slowly added 470 mL of dry morpholine over 10 minutes. After stirring for 50 minutes, 40 mL of ether was added and the solution was washed with 1N HCl. Then the mixture was extracted and the extract acidified and extracted with ether. The ether extract was washed, dried, and evaporated to give P as a colorless mobile oil.

To a solution of alcohol K (80mg), acid P (68mg) and DMAP (4mg) in dry $CH_2Cl_2$ (4 mL) stirred at 0 C under an argon atmosphere was added DCC (44 mg) in dry $CH_2Cl_2$. The mixture was stirred at 0 C for 30 minutes, during which time a white precipitate developed, and then allowed to warm to room temperature and stirred for a further 4 hours. The precipitate was filtered off and the filtrate diluted with $Et_2O$ and washed. The ethereal layer was dried and evaporated in vacuo to give a waxy solid. Chromatography let to pure Q as a colorless, viscous oil (103 mg).

To the amino acid Q (100 mg) was added activated Zinc dust (400 mg) and AcOH (4 mL). The heterogenous mixture was subjected to sonication for 45 minutes, stirred for a further 90-minutes at room temperature, and then poured onto a pad of Celite. The organic material was washed from the Celite pad with $CH_2Cl_2$. The solvent was removed in vacuo, leaving the carboxylic acid as a colorless amorphous solid.

Without purification the crude acid was dissolved in trifluoroacetic acid and allowed to sit at room temperature for one hour. After this time excess TFA was removed in vacuo and the resulting amorphous solid was then subjected to chromatographic purification yielding the trifluoroacetate ammonium salt of the desired compound. Repeated lyophilization of an aqueous solution of the salt resulted in the free amino acid R as a colorless amorphous solid.

To a stirred solution of the corresponding amino acid in anhydrous DMF at room temperature was added diisopropylethylamine followed by pentafluorodiphenylphosphinate (FDPP) in DMF (2 mL). The mixture was stirred for 12 hours, EtO was added, and the ether layer washed, dried, and evaporated. The residual waxy solid was further purified by reverse phase chromatography to give Cryptophycin 51 as a colorless amorphous solid.

To a stirred solution of Cryptophycin 51 (75 mg) in anhydrous dichloromethane (7.5 mL) at 0 C under argon was added a solution of m-chloroperbenzoic acid (50 mg) in dichloromethane (1 mL). After 30 minutes the reaction mixture was allowed to warm to room temperature and stirred for a further 12 hours. The solvent was then removed under reduced pressure to give a 1.8:1 mixture of cryptophycins 52 and 53 (by NMR) as an amorphous solid. The mixture of regioisomeric epoxides was dissolved in minimal acetonitrile and subjected to reverse phase chromatography to separate Cryptophycin 52 (37 mg) and Cryptophycin 53. The product was characterized by NMR.

EXAMPLE 2

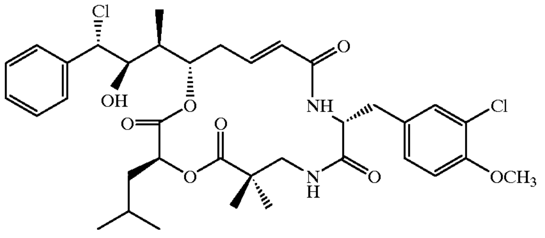

Cryptophycin 55 ("Compound II")

To a solution of Cryptophycin 52 (6 mg) in 0.6 mL of 2:1 1,2-dimethoxyethane/water was added 2 uL of 12 N HCl. The solution was allowed to stir at room temperature for 20 hours, neutralized with potassium carbonate, filtered through a 5 m filter, and evaporated. The acetonitrile-soluble material was purified by reversed-phase HPLC on C18 using 4:1 MeOH/water to obtain 3.0 mg of Cryptophycin 55 (48%). The product was characterized using NMR.

EXAMPLE 3

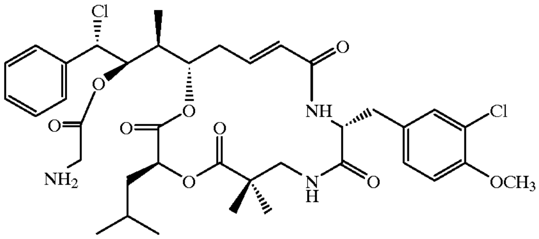

Cryptophycin 55 glycinate ("Compound III")

(a) Preparation of Cryptophycin 55 N-t-Boc-glycinate

To a solution of Cryptophycin 55 (118 mg, 0.167 mmol), N-t-Boc-glycine (44 mg, 0.251 mmol), and 4-dimethylamino pyridine (2.0 mg, 0.0167 mmol) in 490 ml of anhydrous methylene chloride at room temperature was added a solution of 1,3-dicyclohexylcarbodiimide (52 mg, 0.251 mmol) in 67 ml of methylene chloride. After stirring for 50 min, the cloudy white reaction mixture was diluted with ethyl acetate-hexanes (3:1, 1 ml), stirred for 10 min, and filtered through a plug of celite, washing with ethyl acetate-hexanes (3:1). The filtrate and washings were concentrated in vacuo to a colorless oil. Chromatography (19 g of flash silica gel, 3:1/ethyl acetate-hexanes) afforded 138 mg (96%) of the title compound as a white foam:

500 MHz $^1$H NMR ($CDCl_3$) d 7.34 (s, 5H), 7.24 (d, 1H, J=2.0 Hz), 7.23–7.19 (m, 1H), 7.10 (dd, 1H, J=8.4, 2.0 Hz), 6.88 (d, 1H, J=8.4 Hz), 6.79–6.70 (m, 1H), 5.77 (d, 1H, J=13 Hz), 5.50 (d, 1H, J=8.0 Hz), 5.47 (d, 1H, J=9.8 Hz), 4.97 (dd, 1H, J=11, 2.7 Hz), 4.89 (t, 1H, J=10 Hz), 4.83 (d, 1H, J=9.8 Hz), 4.79–4.72 (m, 1H), 4.68 (br s, 1H), 3.91 (s, 3H), 3.66 (dd, 1H, J=18, 5.3 Hz), 3.42–3.35 (m, 2H), 3.21 (dd, 1H, J=13, 4.0 Hz), 3.17 (dd, 1H, J=15, 5.1 Hz), 3.08 (dd, 1H, J=15, 7.6 Hz), 2.66–2.57 (m, 2H), 2.47–2.38 (m, 1H), 1.95 (ddd, 1H, J=14, 12, 4.7 Hz), 1.85–1.77 (m, 1H), 1.75–1.67 (m, 1H), 1.43 (s, 9H), 1.27 (s, 3H), 1.20 (s, 3H), 1.08 (d, 3H, J=7.0 Hz), 1.03 (d, 3H, J=6.7 Hz), 0.98 (d, 3H, J=6.5 Hz).

(b) Preparation of Cryptophvcin 55 glycinate hydrochloride salt

To a solution of the product of step (a) (122 mg, 0.141 mmol) in 471 ml of methylene chloride at room temperature was added a 4.0 M solution of hydrogen chloride in 1,4-dioxane (178 ml, 0.707 mmol). After stirring for lh 20 min, the clear, colorless reaction mixture was concentrated in vacuo to provide 120 mg (99%, corrected for 7 wt% dioxane) of the title compound as a white foam: 500 MHz $^1$H NMR (MeOH-$d_4$) d 7.81 (dd, 1H, J=8.5, 2.2 Hz), 7.46–7.41 (m, 2H), 7.40–7.36 (m, 3H), 7.31 (d, 1H, J=2.1 Hz), 7.20 (dd, 1H, J=8.4, 2.1 Hz), 7.01 (d, 1H, J=8.4 Hz), 6.70 (ddd, 1H, J=15, 13, 3.7 Hz), 5.97 (dd, 1H, J=15, 1.7 Hz), 5.55 (d, 1H, J=9.9 Hz), 5.18 (d, 1H, J=9.9 Hz), 5.14 (dd, 1H, J=10, 2.8 Hz), 4.84 (t, 1H, J=10 Hz), 4.52 (dd, 1H, J=11, 3.7 Hz), 3.87 (s, 3H), 3.78 (d, 1H, J=18 Hz), 3.50 Idd, 1H, J=13, 9.8 Hz), 3.23 (d, 1H, J=18 Hz), 3.20 (dd, 1H, J=14, 3.6 Hz), 3.13 (dd, 1H, J=13, 2.4 Hz), 2.80–2.69 (m, 3H), 2.41–2.32 (m, 1H), 1.99–1.92 (m, 1H), 1.91–1.81 (m, 2H), 1.25 (s, 3H), 1.20 (s, 3H), 1.12 (d, 3H, J=7.0 Hz), 1.06 (d, 3H, J=6.2 Hz), 1.04 (d, 3H, 6.2 Hz).

EXAMPLE 4

Compound IV

IV

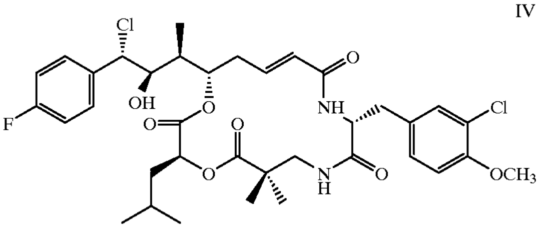

(a) Preparation of Compound IVA

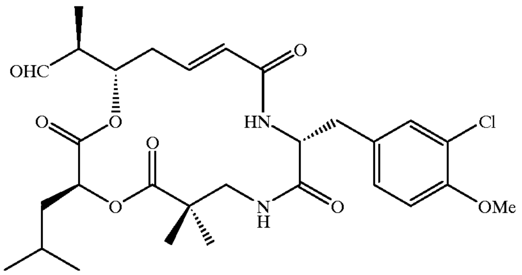

To a solution of Cryptophycin 53 (2.0 g, 2.99 mmol, Barrow, R. A. et al., *J. Am. Chem. Soc.* 1995, 117, 2479–2490) in 30 mL of DME, was added a 2 M aqueous perchloric acid solution (15 mL, 30 mmol) and the resulting mixture was stirred for 6 hours. Upon careful neutralization with saturated $NaHCO_3$ (50 mL) the mixture was extracted with $CH_2Cl_2$ (4×100 mL) and the combined organic layers were dried over $Na_2SO_4$, filtered and concentrated in vacuo. Purification by column chromatography (silica gel, 5% MeOH/$CH_2Cl_2$) gave a mixture of diols (1.5 g) in 72% yield as a 3:1 anti/syn mixture.

To a solution of the diols (1.0 g, 1.46 mmol), in 20 mL of THF and 15 mL of water, was added $NaIO_4$ (1.9 g, 8.9 mmol) and the mixture was stirred under nitrogen overnight. Upon removing the bulk of the THF under reduced pressure, the residue was diluted with water (100 mL) and extracted with $CH_2Cl_2$ (4×50 mL). The combined organic extracts were washed with brine (1×25 mL), dried over $Na_2SO_4$, filtered and concentrated under vacuum. Residual benzaldehyde was removed by dissolving the solid in 100 mL of toluene and subsequently removing the toluene at 40° C. on a rotary evaporator. Two additional evaporations from toluene gave the aldehyde as a yellow foam (0.828 g) in 98% yield. The resulting aldehyde (Compound VA) was used without further purification and was stored at −23° C. for stability reasons:

$[\alpha]^{20}_D$+23.0° (c 0.565, $CHCl_3$); $^1$H NMR (300 MHz, $CDCl_3$) 6 9.64–9.63 (d, 1 H, J=1.4 Hz), 7.28–7.26 (m, 1H), 7.21–7.20 (d, 1 H, J=1.9 Hz), 7.08–7.05 (dd, 1 H, J=7.1, 1.7 Hz), 6.87–6.84 (d, 1 H, J=8.5 Hz), 6.82–6.72 (m, 1H), 5.80–5.75 (d, 1 H, J=15.0 Hz), 5.54–5.51 (d, 1 H, J=7.7 Hz), 5.40–5.33 (m, 1H), 4.85–4.81 (dd, 1 H, J=9.7, 3.2 Hz), 4.78–4.71 (m, 1H), 3.88 (s, 3H), 3.46–3.39 (dd, 1 H. J=13.5, 8.6 Hz), 3.15–3.03 (m, 3H), 2.68–2.35 (m, 3H), 1.82–1.63 (m, 2H), 1.45–1.37 (m, 1H), 1.24 (s, 3H), 1.19–1.16 (d, 3 H, J=7.1 Hz), 1.18 (s, 3H), 0.94–0.92 (d, 3 H, J=6.5 Hz), 0.89–0.87(d, 3 H, J=6.5 Hz); $^{13}$C NMR (63 MHz, $CDCl_3$) δ 200.7, 177.8, 170.6, 170.1, 165.1, 153.9, 141.1, 130.7, 129.8, 128.1, 124.9, 122.3, 112.3, 73.4, 71.1, 56.0, 54.6, 49.9, 46.4, 42.7, 39.2, 36.1, 35.2, 24.7, 22.8, 22.7, 21.3, 10.7; IR ($CHCl_3$) 3422, 2964, 2936, 1755, 1730, 1718, 1678, 1529, 1504, 1487,1474, 1464, 1442, 1320, 1303, 1281, 1259, 1244, 1185, 1151, 1127, 1067 $cm^{-1}$; Anal. ($C_{29}H_{39}ClN_2O_6$): C, H, N.

(b) Preparation of Compound IVB

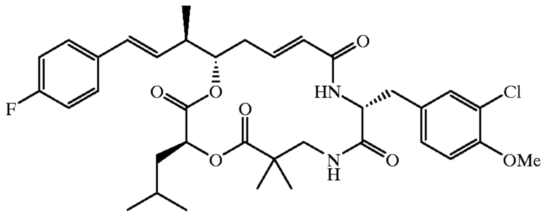

To a slurry of 4-fluorobenzyl triphenylphosphonium bromide (1.4 g, 3.1 mmol) in 15 mL of dry THF at −70° C. under $N_2$ was added a solution of 1.6 M n-butyl lithium in hexanes (1.95 mL, 3.12 mmol) dropwise over 5 minutes. After stirring for 10 minutes, the mixture was allowed to warm to 0° C., at which point it became homogeneous and deep red-brown in color. This red solution was added dropwise via a double-tipped needle to aldehyde of Example 5, step (a) (1.5 g, 2.6 mmol, Compound IVA) in 15 mL of THF at −70° C. The reaction mixture was allowed to stir at −70° C. for 30 minutes, then warmed to room temperature over 45 minutes. Saturated $NH_4Cl$ (10 mL) was added followed by EtOAc (150 mL). The EtOAc solution was washed with water (2x25 mL) and brine (1x20 mL), dried over $MgSO_4$, filtered through a pad of silica gel and evaporated to a yellow foam. Chromatography (30–100% EtOAc/hexanes) provided the styrene (1.24 g) in 71% yield as a white foam and as an E/Z mixture.

The mixture of isomers was dissolved in benzene (40 mL) and heated to reflux in the presence of 1,1'-azobis (cyclohexanecarbonitrile) (VAZO) (0.05 g, 0.20 mmol) and thiophenol (0.076 mL, 0.74 mmol) for 24 hours. After concentration the residue was purified by radial PLC (20–80% EtOAc/hexanes) to give the E isomer (1.06 g) as a white foam containing triphenylphosphine oxide by NMR. A 0.15 g sample was purified by reverse-phase HPLC (60:40) $CH_3CN$:$H_2O$ to give 0.092 g of a pure analytical sample: $[\alpha]^{20}_D$+27.49 ° (c 1.05, $CHCl_3$ ); $^1H$ NMR (300 MHz, $CDCl_3$) δ 7.31–6.96 (m, 7H), 6.85–6.83 (d, 1 H, J=8.5 Hz), 6.81–6.74 (m, 1H), 6.39–6.34 (d, 1 H, J=15.8 Hz), 5.96–5.88 (dd, 1 H, J=8.8, 15.8 Hz), 5.77–5.72 (d, 1 H, J=15.2 Hz), 5.49–5.47 (d, 1 H, J=7.7 Hz), 5.07–5.02 (m, 1H), 4.86–4.83 (dd, 1 H, J=9.2, 2.5 Hz), 4.82–4.73 (m, 1H), 3.87 (s, 3H), 3.45–3.38 (dd, 1 H, J=13.4, 8.5 Hz), 3.14–3.08 (m, 3H), 2.57–2.52 (m, 2H), 2.43–2.34 (m, 1H), 1.71–1.58 (m, 2H), 1.36–1.29 (m, 1H), 1.22 (s, 3H), 1.16 (s, 3H), 1.14–1.11 (d, 3 H, J=6.9 Hz), 0.78–0.73 (m, 6H); $^{13}C$ NMR (63 MHz, $CDCl_3$) δ 177.8, 170.5, 170.3, 165.1, 160.2, 154.0, 142.0, 137.6, 132.9, 132.8, 130.8, 130.4, 130.0, 129.6, 128.2, 127.6, 127.5, 124.6, 122.4, 115.6, 115.2, 112.2, 71.3, 56.0, 54.4, 46.4, 42.7, 42.1, 39.5, 36.4, 35.2, 24.5, 22.8, 22.6, 21.2, 17.2; IR (KBr) 3421, 3289, 2862, 2933, 1751, 1722, 1678, 1604, 1534, 1509, 1259, 1228, 1149, 1066, 1024, 1011, 971, 815 $cm^{-1}$; Anal. ($C_36H_{44}ClFN_2O_7$) C, H, N.

(c) Preparation of Compound IVC

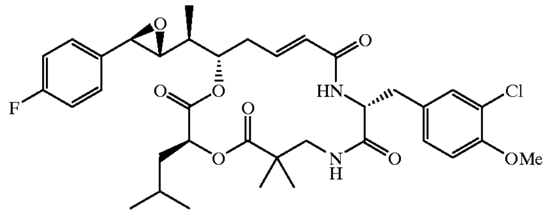

To a solution of the above styrene (0.906 g, 1.35 mmol) in 4.5 mL $CH_2Cl_2$ at 0° C. was added 3-chloroperoxybenzoic acid (0.25 g, 1.45 mmol) and toluene (2.2 mL) and stirring continued at 0° C. for 30 minutes. The ice-bath was removed and the reaction allowed to stir at room temperature for 23 hours. After diluting with 20 mL of $CH_2Cl_2$ , the reaction mixture was washed with 10% $Na_2S_2O_5$ (1x10 mL), water (1x10 mL), saturated $NaHCO_3$ (1x10 mL) and brine (1x10 mL) and finally was dried over $Na_2SO_4$. Filtration and concentration gave 0.814 g of the product as a mixture of the b/a epoxides. A 0.23 g portion was purified by reverse-phase HPLC ($CH_3CN/H_20$) to give 0.073 g of the P-epoxide (Compound IVC) as a white foam: $[\alpha]^{20}_D$+25.6° (c 0.626, $CHCl_3$ ); $^1H$ NMR (300 MHz, $CDCl_3$) δ 7.26–7.03 (m, 7H), 6.85–6.83 (d, 1 H, J=8.4 Hz), 6.82–6.72 (m, 1 H), 5.74–5.69 (d, 1 H, J=15.2 Hz), 5.44–5.42 (d, 1 H, J=7.9 Hz), 5.23–5.18 (m, 1H), 4.85–4.81 (dd, 1 H, J=9.7, 2.9 Hz), 4.77–4.73 (m, 1H), 3.88 (s, 3H), 3.66 (s, 1H), 3.46–3.39 (dd, 1 H, J=13.5, 8.8 Hz), 3.12–3.07 (m, 3H), 2.89–2.87 (dd, 1 H, J=1.5, 7.7 Hz), 2.60–2.54 (m, 1H), 2.49–2.41 (m, 1H), 1.81–1.65 (m, 3H), 1.34–1.25 (m, 1H), 1.22 (s, 3H), 1.16 (s, 3H), 1.15–1.13 (d, 3 H, J=7.0 Hz), 0.87–0.82 (m, 6H); $^{13}C$ NMR (63 MHz, $CDCl_3$) δ 177.8, 170.3, 164.9, 164.7, 154.0, 141.6, 137.8, 132.4, 130.7, 129.6, 128.1, 127.3, 127.2, 124.6, 122.4, 115.8, 115.5, 112.2, 75.8, 71.0, 63.0, 58.2, 56.0, 54.4, 46.3, 42.7, 40.4, 39.3, 36.7, 35.2, 23.5, 22.8, 22.76, 22.6, 21.1, 13.3; IR ($CHCl_3$) 3426, 3030, 3006, 2964, 2936, 1752, 1711, 1683, 1608, 1514, 1485, 1442, 1303, 1281, 1259, 1188, 1155, 1067, 838 $cm^{-1}$; Anal. ($C_{36}H_{44}ClFN_20_8$) C, H, N.

(d) Preparation of Compound IV

A 4 M solution of HCl in dioxane (0.4 mL, 1.6 mmol) was added dropwise over 5 minutes to a −70° C. solution of β-epoxide (Compound VC) (0.44 g, 0.64 mmol) in 30 mL $CH_2Cl_2$. Following 2 additional hrs of stirring at −70° C., the solution was concentrated in vacuo. The crude product was purified by radial PLC (silica gel, 30–50–100% EtOAc/$CH_2Cl_2$) followed by reverse phase HPLC (50:50) $CH_3CN$:$H_2O$ to give 0.152 g (33%) of the desired chlorohydrin (Compound V) as a white-foam: $[\alpha]^{20}_D$+60.0 ° (c 2. 62, $CHCl_3$ )H; $^1$ NMR (300 MHz, $CDCl_3$) δ 7.41–7.05 (m, 7H), 6.87–6.84 (d, 1 H, J=8.4 Hz), 6.83–6.77 (m, 1H), 5.80–5.75 (d, 1 H, J=15.4 Hz), 5.52–5.49 (d, 1 H, J=7.8 Hz), 5.13–5.21 (m, 1H), 4.94–4.90 (dd, 1H, J=9.7,3.2 Hz), 4.75–4.72 (m, 1H), 4.67–4.63 (d, 1 H, J=9.5 Hz), 4.00–3.95 (m, 1H), 3.89 (s, 3H), 3.42–3.35 (dd, 1H, J=8.3, 13.5 Hz), 3.20–3.02 (m, 3 H), 2.71–2.65 (m, 1H), 2.49–2.37 (m, 2H), 1.82–1.63 (m, 2 H), 1.51–1.38 (m, 2H), 1.23 (s, 3H), 1.17 (s, 3H), 1.04–1.02 (d, 3 H, J=7.0 Hz). 0.97–0.85 (m, 6H); $^{13}C$ NMR (63 MHz, $CDCl_3$) δ 177.6, 170.5, 170.3, 165.3, 160.7, 153.9, 142.2, 137.5, 134.5, 130.8, 129.8, 129.7, 128.2, 124.6, 122.2, 76.1, 74.0, 71.1, 61.4, 56.1, 54.5, 46.4, 42.7, 39.6, 38.4, 36.3, 35.1, 24.8, 23.0, 22.9, 22.7, 21.5, 8.6; IR ($CHCl_3$) 3423, 2965, 2935, 2873, 1751, 1715, 1679, 1607, 1528, 1504, 1485, 1464, 1442, 1302, 1281, 1193, 1159, 1152, 1127, 1067 $cm^{-1}$; Anal. ($C_{36}H_{45}Cl_2N_20_8$) C, H, N. $IC_{50}$ (CEM cell line) 0.033 nM.

EXAMPLE 5

Compound V

V

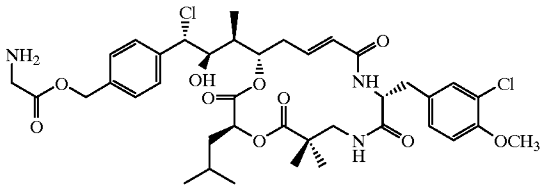

(a) Preparation of Compound VA (VA)

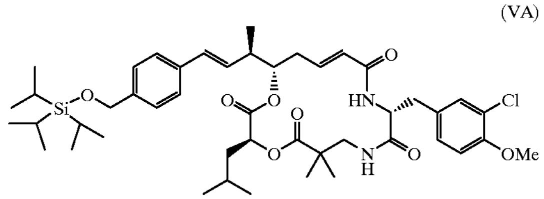

To 4-(triisopropylsiloxymethyl)benzyl triphenylphosphonium bromide (7.6 g, 12.2 mmol) in 100 mL of THF at −50° C. was added dropwise 8.0 mL of a 1.5 M solution of n-butyllithium (8.1 mL, 12.2 mmol). The mixture was warmed slowly to room temperature and stirred for an additional 30 min. To aldehyde of Example 4, step a (Compound IVA) (2.95 g, 5.1 mmol), in 100 mL of THF and at −78° C., was added dropwise the red ylide solution via a double tipped needle. The resulting mixture was stirred at −78° C. for 3 h and at room temperature for 45 min. Saturated $NH_4Cl$ (100 mL) was added along with ethyl acetate (100 mL), the layers separated and the aqueous one extracted with ethyl acetate (2x50 mL). The combined organic layers were washed with water (3x40 mL) and brine, dried over $MgSO_{41}$ filtered and concentrated in vacuo. The resulting yellow residue was purified using column chromatography (silica gel, 10–20–50% EtoAc/hexanes) to give 3.6 g (84%) of the desired styrene as a white solid and as a mixture of E:Z isomers.

The mixture of isomers (7.3 g, 8.7 mmol) was dissolved in 240 mL of benzene and heated to reflux in the presence of 1,1'-azobis(cyclohexanecarbonitrile) (VAZO) (0.32 g, 0.87 mmol) and thiophenol (3.7 mL, 4.0 mmol). Following 5 h of reflux, the solution was concentrated and the residue purified by column chromatography (silica gel, 5–50% EtOAc/hexanes) to give 6.7 g (92%) of the E isomer as a white solid: $[\alpha]^{20}{}_D$+31.9° (c1.0, $CHCl_3$); $^1H$ NMR (300 MHz, $CDCl_3$) δ 7.3–7.22 (m, 5H), 7.20–7.19 (d, 1 H, J=1.95 Hz), 7.07–7.04 (dd, 1 H, J=8.4, 2.0 Hz), 6.85–6.82 (d, 1 H, J 8.5 Hz), 6.8–6.7 (m, 1H), 6.4–6.38 (d, 1 H, J=15.8 Hz), 6.02–5.94 (dd, 1 H, J=15.8, 8.8 Hz), 5.77–5.72 (d, 1 H, J=14.9 Hz), 5.56–5.54 (d, 1 H, J=7.9 Hz), 5.1–4.7 (m, 5 H), 3.9 (s, 3H), 3.45–3.37 (dd, 1 H, J=13.5, 8.5 Hz), 3.2–3.0 (m, 3H), 2.6–2.3 (m, 3H), 1.7–1.5 (m, 2H), 1.4–1.0 (m, 31H), 0.75–0.71 (t, 6 H, J=6.1 Hz); $^{13}C$ NMR (63 MHz, $CDCl_3$) δ 177.8, 170.5, 170.4, 165.2, 153.9, 142.1, 141.1, 135.2, 131.5, 130.8, 129.7, 129.6, 128.1, 125.9, 124.5, 122.4, 112.2, 77.0, 71.4, 64.7, 56.0, 54.4, 46.4, 42.7, 42.2, 39.4, 36.5, 35.3. 24.5, 22.8, 22.6, 22.5, 21.2, 17.9, 17.2, 11.9; IR ($CHCl_3$) 3423, 2962, 2945, 2867, 1746, 1712, 1681, 1652, 1528, 1503, 1485, 1473, 1464, 1303, 1259 $cm^{-1}$; Anal. ($C_{46}H_{67}ClN_2O_8Si$): C, H, N.

(b) Preparation of Compound VB (VB)

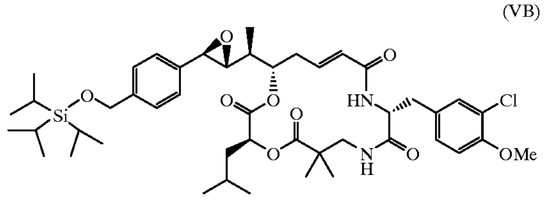

3-Chloroperoxybenzoic acid (0.27 g, 1.59 mmol) was added to a 0° C. solution of slyrene of Example 5, step a (Compound VA) (1.25 g , 1.49=mol) in 20 mL of $CH_2Cl_2$. The solution was stirred for 1 h at 0° C. and overnight at room temperature. It was concentrated in vacuo and the resulting epoxides separated by reverse phase HPLC to yield 0.67 g of the D epoxide (Compound VIB)(57%) as a white solid: $[\alpha]^{20}{}_D$+20.9 C (c 0.765, $CHCl_3$); $^1H$ NMR (300 MHz, $CDCl_3$) δ 7.35–7.33 (d, 2 H, J=7.8 Hz), 7.26–7.2 (m, 4H), 7.05–7.02 (bd, 1 H, J=8.2 Hz), 6.84–6.81 (d, 1 H, J=8.4 Hz), 6.81–6.65 (m, 1 H), 5.8–5.65 (m, 2H), 5.25–5.15 (m, 1H), 4.9–4.7 (m, 4H), 3.9 (s, 3H), 3.7 (s, 1H), 3.46–3.42 (dd, 1 H, J=13.4, 8.8 Hz), 3.15–3.0 (m, 3H), 2.93–2.9 (d, 1 H, J=7.3 Hz), 2.6–2.4 (m, 2H), 1.8–1.6 (m, 3H), 1.4–1.0 (m, 31H), 0.83–0.79 (t, 6 H, J=5.3 Hz); ,$^3C$ NMR (63 MHz, $CDCl_3$) δ 177.7, 170.5, 170.4, 165.1, 153.9, 142.1, 141.6, 136.7, 135.1, 130.7, 129.8, 128.1, 125.9, 125.5, 124.6, 122.3, 112.2, 75.9, 71.0, 64.6, 63.0, 58.9, 56.0, 54.6, 46.3, 42.7, 40.5, 39.2, 36.8, 35.2. 24.2, 22.8, 22.7, 22.6, 18.0, 13.4, 11.9; IR ($CHCl_3$) 3424, 2962, 2945, 2867, 1751, 1712, 1682, 1528, 1503, 1485, 1473, 1464, $cm^{-1}$; Anal. ($C_4$6H6, $ClN_2O_9Si$): C, H, N. $IC_{50}$ (CEM cell line) 0.7 nM.

(c) Preparation of Compound VC

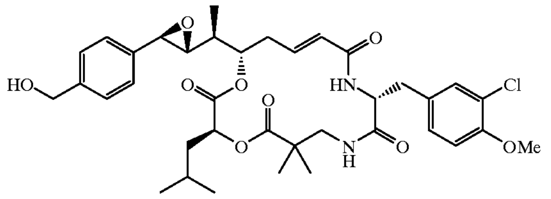

Tetrabutylammonium fluoride (0.14 mL, 0.14 mmol), as a 1.0 M solution in THF, was added dropwise to a 0° C. solution of the 0 epoxide of Example 5, step b (Compound VIB)(0.1 g, 0.117 mmol) in 3.5 mL of THF. The solution was allowed to warm up to room temperature and stirring was continued for another 20 min, followed by the addition of water (10 mL) and ethyl acetate (20 mL). The layers were separated and the aqueous one was extracted with $CH_2Cl_2$ (3x20 mL). The combined organic layers were dried over anhydrous $Na_2SO_4$, filtered and concentrated in vacuo to yield the free alcohol. Purification by column chromatography (silica gel, 70–100% EtOAc-hexanes) yielded 0.068 g (84%) of the pure alcohol as a white solid: $[\alpha]^{20}{}_D$+26.2 ° (c0.435, $CHCl_3$); $^1H$ NMR (300 MHz, $CDCl_3$) δ 7.39–7.36 (d, 2 H, J=7.8 Hz), 7.26–7.23 (d, 3 H, J 9.1 Hz), 7.18 (s, 1H), 7.05–7.02 (d, 1 H, J=8.5 Hz), 6.85–6.82 (d, 1 H, J=8.2 Hz), 6.82–6.7 (m, 1H), 5.72–5.67 (d, 1 H, J=15.1 Hz), 5.55–5.52 (d, 1 H, J=7.8 Hz), 5.22–5.17 (m, 1H), 4.85–4.7 (m, 4H), 3.9 (s, 3H), 3.7 (s, 1H), 3.45–3.38 (dd, 1 H, J=13.4, 9.3 Hz), 3. 2–3.0 (m, 3H), 2.92–2.89 (d, 1 H, J=7.6 Hz), 2.65–2.4 (m, 2H), 1. 8–1.6 (m, 4H), 1. 4–1.2 (m, 1H), 1.22 (s, 3H), 1.16 (s, 3H), 1.16–1.13 (d, 3 H, J=7.2 Hz), 0.86–0.82 (t, 6 H, J=6.5 Hz); $^{13}C$ NMR (63 MHz, $CDCl_3$) δ 177.8, 171.0, 170.4, 165.5, 153.8, 141.5, 141.4, 135.7, 133.5, 130.6, 130.0, 128.0, 127.1, 125.6, 124.6, 122.2, 112.3, 77.2, 76.5, 76.0, 71.0, 64.2, 63.1, 58.8, 56.0, 54.7, 46.3, 42.7, 40.5, 39.3, 36.9, 35.1, 24.5, 22.7, 22.5, 22.1, 13.4; IR ($CHCl_3$) 3422, 2992, 2963, 2936, 2874, 1751, 1713, 1682, 1651, 1504, 1486, 1303, 1259, 1186, 1165, 1151, 1067 $cm^{-1}$; FAB HRMS [M+H] cacld for ($C_{37}H_{48}ClN_2O_9$) 699.3048, found 699.3054. $IC_{50}$ (CEM cell line) 0.004 nM.

(d) Preparation of Compound VD

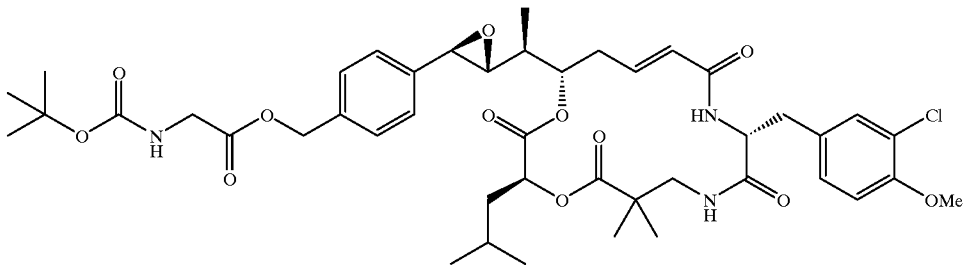

To a 0° C. solution of alcohol of Example 5, step c (Compound VC) (0.08 g, 0.114 mmol), N-(tert-butoxycarbonyl)glycine (0.034 g, 0.194 mmol) and 4-dimethylaminopyridine (DMAP) (0.004 g, 0.034 mmol) in 2.0 mL $CH_2Cl_2$ was added 1,3-dicyclohexylcarbodiimide (DCC) (0.040 g, 0.194 mmol). The mixture was stirred at 0° C. for 10 min and at room temperature for 45 min, filtered and concentrated in vacuo. The resulting residue was purified using column chromatography (silica gel, 70–80% EtOAc/hexanes) to give 0.07 g (72%) of the ester as a white solid: [a]2%D +18.5 ° (c 0.65, $CHCl_3$); $^1$H NMR (300 MHz, $CDCl_3$) δ 7.4–7.2 (m, 6H), 7.11–7.08 (dd, 1 H, J=8.4, 1.8 Hz), 6.9–6.87 (d, 1 H, J=8.4 Hz), 6.86–6.7 (m, 1H), 5.78–5.73 (d, 1 H, J=15.2 Hz), 5.64–5.62 (d, 1 H, J=7.4 Hz), 5.3–5.22 (m, 1H), 5.22 (s, 2H), 5.1–5.0 (bs, 1H), 4.9–4.7 (m, 2H), 4.0–3.99 (d, 2 H, J=5.4 Hz), 3.9 (s, 3H), 3.73–3.72 (d, 1 H, J=1.0 Hz), 3.5–3.43 (dd, 1 H, J=13.4, 8.6 Hz), 3.2–3.0 (m, 3H), 2.95–2.92 (d, 1 H, J=6.4 Hz), 2.65–2.4 (m, 2H), 1.8–1.6 (m, 3H), 1.5 (s, 9H), 1.45–1.3 (m, 1H), 1.26 (s, 3H), 1.2 (s, 3H), 1.2–1.17 (d, 3 H, J=8.7 Hz), 0.9–0.86 (t, 6 H, J=6.3 Hz); $^{13}$C NMR (63 MHz, $CDCl_3$) δ 177.7, 170.6, 170.3, 170.2, 165.1, 155.6, 153.8, 141.4, 137.1, 135.6, 130.6, 129.9, 128.6, 128.0, 125.7, 124.7, 122.2, 112.2, 79.9, 75.8, 70.9, 66.4, 63.1, 58.5, 56.0, 54.7, 48.9, 46.3, 42.7, 42.4, 40.5, 39.3, 36.8, 35.2, 28.2, 24.5, 22.8, 22.7, 22.6, 21.2, 13.5; Anal. ($C_{44}H_58ClN_301_2$): C, H, N. $IC_{50}$ (CEM cell line) 0. 0055 nM.

(e) Preparation of Compound VE

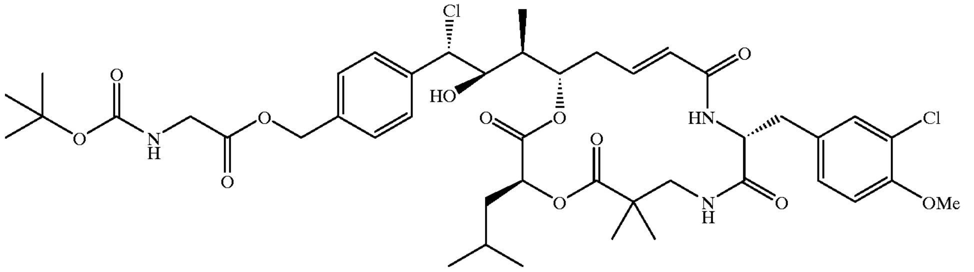

Trimethylsilyl chloride (0.09 mL, 0.75 mmol) was added to a −60° C. solution of the above β-epoxide (0.16 g, 0.187 mmol) in 5.0 mL of $CHCl_3$. Following 2 h of stirring between −60° C. to −40° C. an additional 0.09 mL of TMSCl was added and stirring continued for 3 h. The solution was allowed to warm up to room temperature, concentrated and purified by reverse phase preparative HPLC (55:45) $CH_3CN:H_2O$ to separate the two resulting chlorohydrins. This purification gave 0.058 g (35%) of the desired chlorohydrin: $[\alpha]^{20}_D$+50.5° (c 1.075, $CHCl_3$ ); $^1$H NMR (300 MHz, $CDCl_3$) 6 7042–7.2 (m, 6H), 7.13–7.09 (dd, 1 H, U=8.4, 1.8 Hz), 6.9–6.87 (d, 1 H, U=8.4 Hz), 6.85–6.7 (m, 1H), 5.9–5.8 (m, 2H), 5.2 (s, 3H), 5.15–5.05 (m, 1H), 5.0–4.9 (m, 1 H), 4.8–4.72 (m, 1H), 4.71–4.68 (d, 1 H. U=9.7 Hz), 4.07–4.03 (d, 1 H, U=9.3 Hz), 3.99–3.97 (d, 2 H. U=5.5 Hz), 3.9 (5, 3H), 3.44–3.37 (dd, 1 H. U=13.6, 8.3 Hz), 3.23–3.14 (m, 2H), 3.08–3.0 (dd, 1 H, U=14.5, 8.0 Hz), 2.75–2.4 (m, 3H), 2.0–1.7 (m, 3H), 1.5 (5, 10H), 1.26 (s, 3H), 1.21 (, 3H), 1.08–1.06 (d, 3 H. U=7.0 Hz), 0.977–0.963 (d, 3 H, U=4.0 Hz), 0.956–0.942 (d, 3 H, U=4.1 Hz); $^3$C NMR (63 MHz, $CDCl_3$) 177.5, 170.5, 170.2, 170.1, 165.3, 153.9, 142.2, 139.0, 138.3, 136.1, 130.8, 129.9, 128.7, 128.2, 128.1, 124.5, 122.3, 112.2, 80.0, 76.1, 73.9, 71.1, 66.2, 61.7, 56.1, 54.6, 46.4, 42.7, 42.3, 39.6, 38.4, 36.3, 35.1, 28.2, 24.8, 23.0, 22.9, 22.7, 21.5, 8.6; IR ($CHCl_3$) 3428, 3009, 2966, 2935, 1750, 1714, 1683, 1504, 1486, 1369, 1259, 1193, 1162, 1127, 1067; FAB HRMS [M+H] cacld for ($C_{44}H_{60}ClN_3O_{12}$) 892.3554, found 892.3565. $IC_{50}$ (CEM cell line) 0.013 nM.

(f) Preparation of Compound V

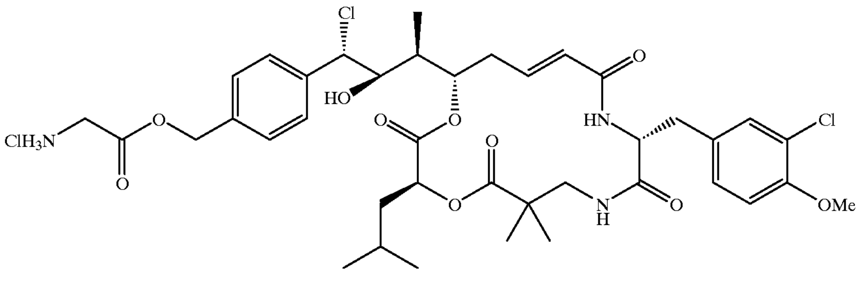

A 4 M solution of hydrogen chloride in 1,4-dioxane (0.08 mL, 0.33 mmol) was added to a solution of the glycinate (0.058 g, 0.065 mmol) in 0.2 mL of $CH_2Cl_2$. The resulting mixture was stirred at room temperature for 3 h, concentrated in vacuo and maintained under vacuum for 3 days to remove the 1,4-dioxane thus giving the desired hydrochloride salt in quantitative yield: $[\alpha]^{20}{}_D$+26.20 (c 0.58, MeOH ); $^1$H NMR (500 MHz, $CD_3OD$) 6 7.48–7.42 (q, 4 H, J=11.2 Hz), 7;31–7.3 (d, I H, J=2.0 Hz), 7.21–7.19 (dd, 1 H, J=8.5, 2.0 Hz), 7.01–7.0 (d, 1 H, J=8.4 Hz), 6.8–6.7 (m, 1H), 6.0–5.95 (dd, 1 H, J=15.2, 1.5 Hz), 5.3 (d, 2 H, J=1.3 Hz), 5.16–5.1 (m, 1H), 5.09–5.07 (dd, 1 H, J=10.0, 3.6 Hz), 4.84–4.82 (d, 1 H, J=9.8 Hz), 4.54–4.51 (dd, 1 H, J=11.3, 3.7 Hz), 4.05–4.03 (dd, 1 H, J=9.5, 1.8 Hz), 3.9 (s, 2H), 3.86 (s, 3H), 3.5–3.47 (d, 1 H, J=13.5 Hz), 3.22–3.18 (dd, 1 H, J=14.5, 3.6 Hz), 3.14–3.11 (d, 1 H, J 13.5 Hz), 2.8–2.77 (d, 1 H, J=14.4 Hz), 2.78–2.75 (m, 2H), 2.55–2.35 (m, 2H), 1.9–1.55 (m, 4H), 1.4–1.3 (m, 1H), 1.24 (s, 3H), 1.2 (s, 3H), 1.04–1.03 (d, 3 H, J 7.0 Hz), 1.02–1.0 (t, 6 H, J=7.2 Hz); $^{13}$C NMR (75 MHz, $CDCl_3$) 6 178.9, 173.8, 171.9, 168.3, 155.3, 144.2, 141.8, 136.7, 132.3, 131.5, 129.75, 129.7, 129.4, 125.2, 123.3, 113.5, 77.2, 74.7, 72.6, 68.5, 63.5, 57.6, 56.7, 47.6, 44.1, 41.1, 40.4, 37.9, 36.5, 26.3, 23.6, 23.5, 22.2, 9.0; IR (KBr) 3412, 2961; 2935, 1752, 1722, 1669, 1504, 1473, 1279, 1259, 1207, 1151, 1126, 1065 cm$^{-1}$; FAB HRMS [M-Cl] cacld for ($C_{39}H_{52}Cl_2N_3O_{10}$) 792.3030, found 792.3020.

We claim:

1. A method for controlling fungal growth comprising administering a therapeutically effective amount of a compound selected from the group consisting of Compound I, Compound II, Compound III, Compound IV and Compound V Compound I: I

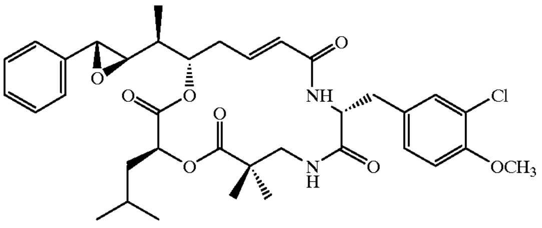

-continued

Compound II: II

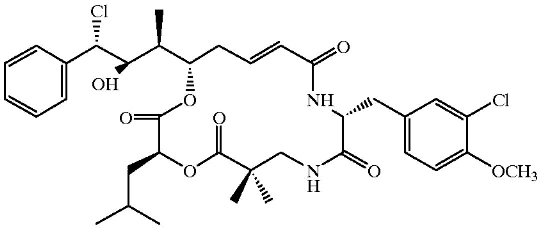

Compound III: III

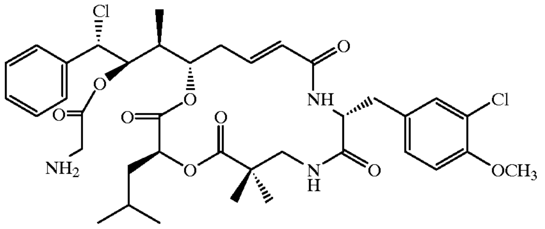

Compound IV: IV

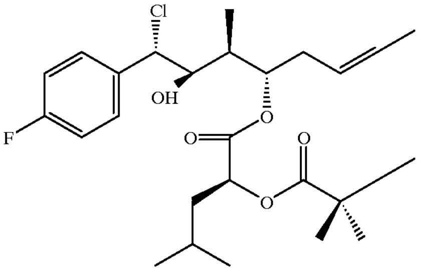

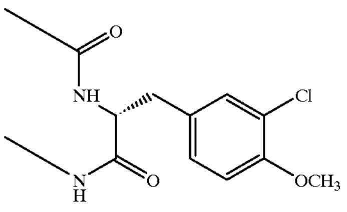

-continued

Compound V: V

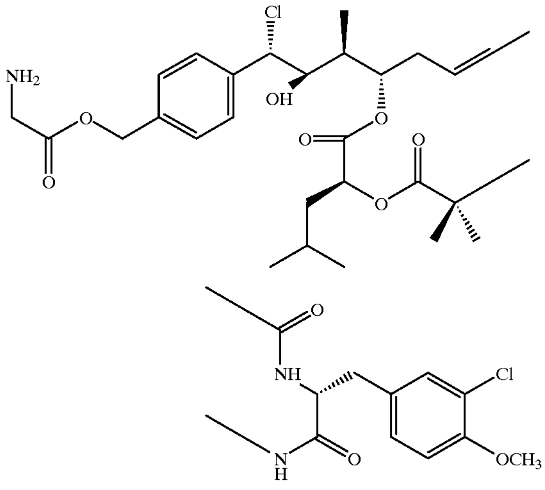

or a pharmaceutically acceptable salt thereof.

2. A method of claim 1 wherein the compound is Compound I.

3. A method of claim 1 wherein the compound is Compound II.

4. A method of claim 1 wherein the compound is Compound III.

5. A method of claim 1 wherein the compound is Compound IV.

6. A method of claim 1 wherein the compound is Compound V.

7. A method of claim 1 wherein the fungal infection is a *Cryptococcus neoformans* infection.

8. A method for providing mdr-inhibitor activity of a fungus comprising administering a therapeutically effective amount of a compound of the formula IA:

IA

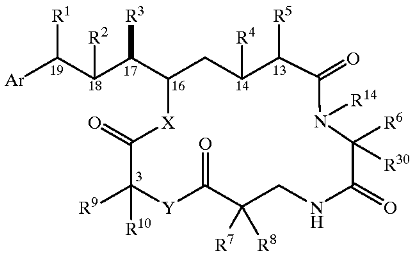

wherein

Ar is phenyl or any simple unsubstituted or substituted aromatic or heteroaromatic group;

$R^1$ is halogen, SH, amino, monoalkylamino, dialkylamino, trialkylammonium, alkylthio, dialkylsulfonium, sulfate, or phosphate;

$R^2$ is OH or SH; or $R^1$ and $R^2$ may be taken together to form an epoxide ring, and aziridine ring, an episulfide ring, a sulfate ring, or monoalkylphosphate ring; or $R^1$ and $R^2$ may be taken together to form a second bond between $C_{18}$ and $C_{19}$;

$R^3$ is a lower alkyl group;

$R^4$ is H;

$R^5$ is H;

$R^4$ and $R^5$ may be taken together to form a second bond between $C_{13}$ and $C_{14}$;

$R^6$ is benzyl, hydroxybenzyl, alkoxybenzyl, halohydroxybenzyl, dihalohydroxybenzyl, haloalkoxybenzyl, or dihaloalkoxybenzyl group, a substituent selected from the group consisting of B-ring heteroaromatic, substituted heteroaromatic, B-ring (CI $-C_6$)alkyl, ($C_3$–$C_8$)cycloalkyl, substituted $C_3$–CS cycloalkyl, substituted ($C_1$–$C_6$)alkyl, a group of the formula III':

III'

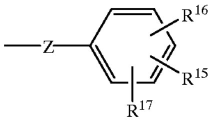

and a group of the formula III'':

III''

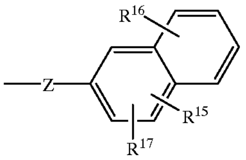

;

$R^7$ is H or a lower alkyl group;

$R^8$ is H or a lower alkyl group;

$R^9$ is H or a lower alkyl group;

$R^{10}$ is H or a lower alkyl group;

$R^{14}$ is H or a lower alkyl group;

$R^{15}$, $R^{16}$, and $R^{17}$ are each independently selected from the group consisting of hydrogen, $OR^{18}$, halo, $NH_2$, $NO_2$, $OPO_4H_2$, $OR^{19}$phenyl, and ZZ;

$R^{18}$ is $C_1$–$C_6$ alkyl;

$R^{19}$ is $C_1$–$C_6$ alkyl;

$R^{30}$ is $C_1$–$C_6$ alkyl;

n is 0, 1, or 2;

p is 0, 1, or 2;

m is 0, 1, or 2;

X is O, NH or alkylamino;

Y is C, O, NH, S, SO, $SO_2$ or alkylamino;

Z is selected from the group consisting of $-(CH_2)_n-$, $-(CH_2)_p-O-(CH_2)_m-$ and ($C_3$–$C_5$)cycloalkyl;

ZZ is selected from the group consisting of an aromatic group and a substituted aromatic group; or a pharmaceutically acceptable salt or solvate thereof.

9. A method according to claim 8 wherein said compound of formula IA is either Cryptophycin 1 or Cryptophycin 42.

10. A method according to claim 8 wherein said compound of formula IA is either Cryptophycin 52 or Cryptophycin 55.

11. An antifungal composition comprising at least five percent (5%) by weight of a compound selected from the group consisting of Compound II, Compound III, Compound IV and Compound V:

Compound I:
I
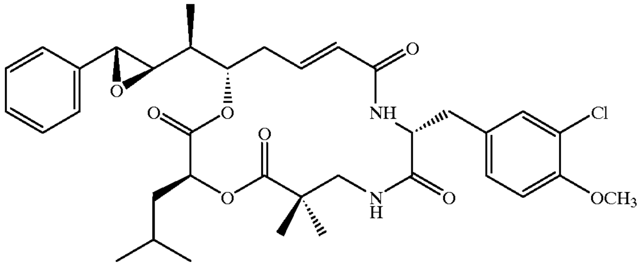
Compound II:
II
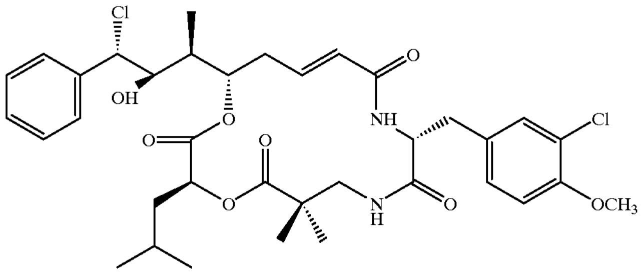
Compound III:
III
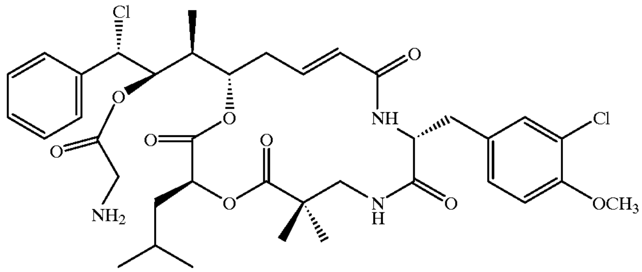
Compound IV:
IV
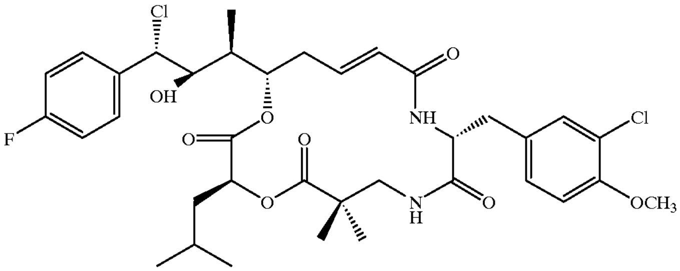
Compound V:
V
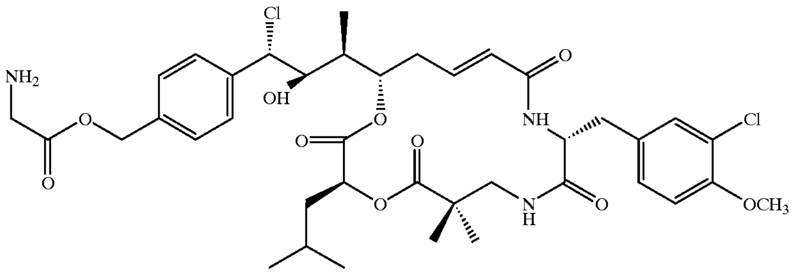

or a pharmaceutically acceptable salt thereof, in admixture with one or more pharmaceutically acceptable carriers, diluents or excipients therefor.

12. A composition according to claim 11 wherein said compound is Compound II.

13. A composition according to claim 11 wherein said compound is Compound III.

14. A composition according to claim 11 wherein said compound is Compound IV.

15. A composition according to claim 11 wherein said compound is Compound V.

16. A method for controlling a mycotic infection comprising administering a therapeutically effective amount of a compound selected from the group consisting of Compound I, Compound II, Compound im, Compound IV and Compound V:

Compound I:

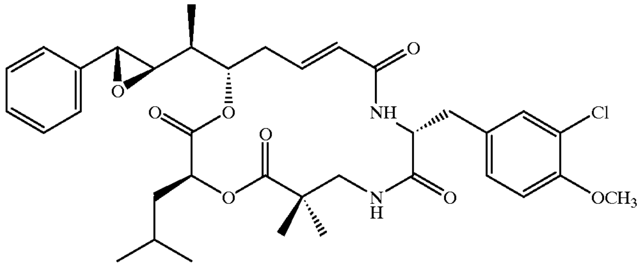

I

Compound II:

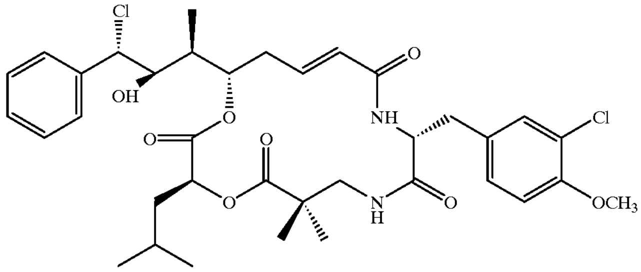

II

Compound III:

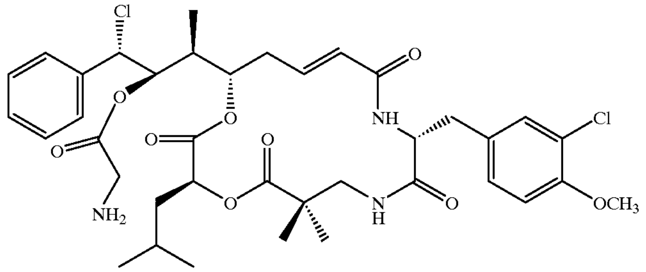

III

Compound IV:

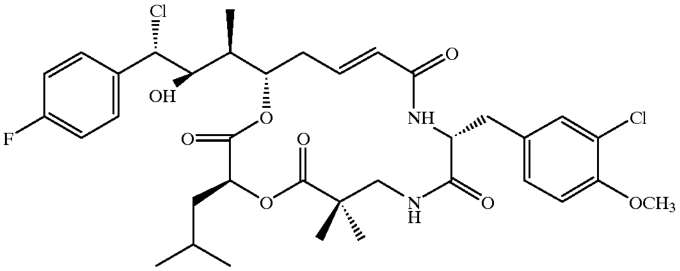

IV

-continued

Compound V:

V

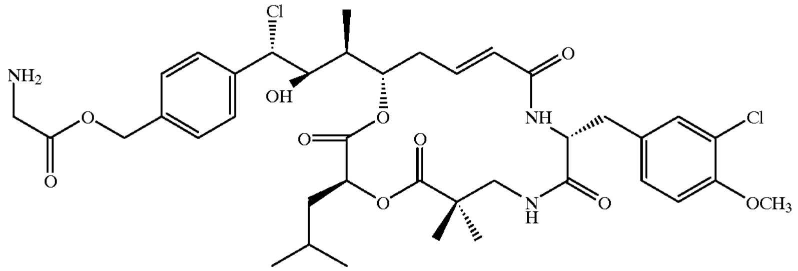

or a pharmaceutically acceptable salt thereof.

17. A method according to claim 16 wherein said compound is Compound I.

18. A method according to claim 16 wherein said compound is Compound I.

19. A method according to claim 16 wherein said compound is Compound III.

20. A method according to claim 16 wherein said compound is Compound IV.

21. A method according to claim 16 wherein said compound is Compound V.

22. A method for controlling a yeast infection comprising administering a therapeutically effective amount of a compound selected from the group consisting of Compound I, Compound II, Compound III, Compound IV and Compound V:

I

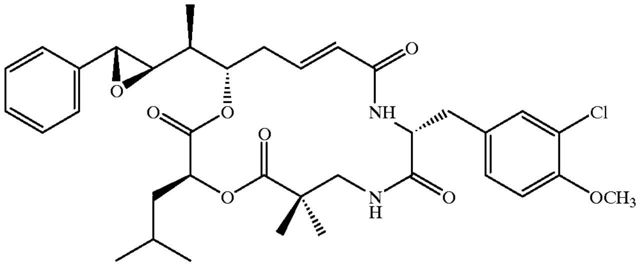

Compound II:

II

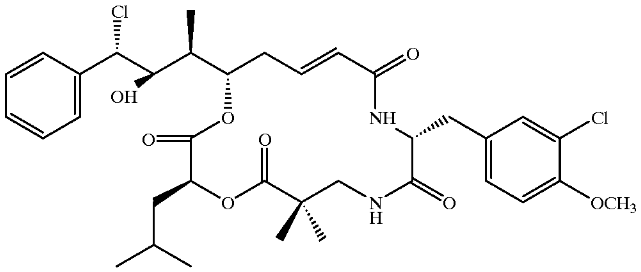

Compound III:

III

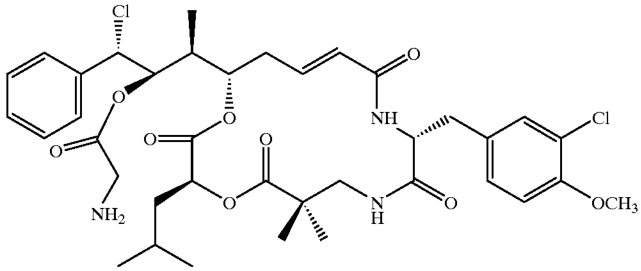

-continued

Compound IV:

IV

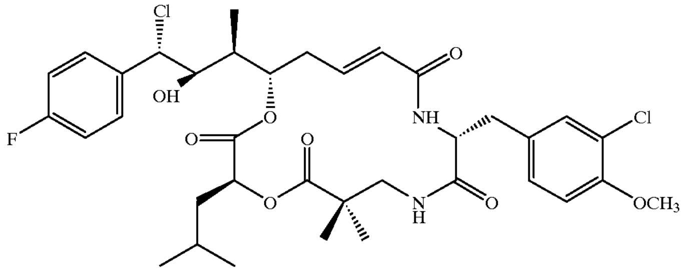

Compound V:

V

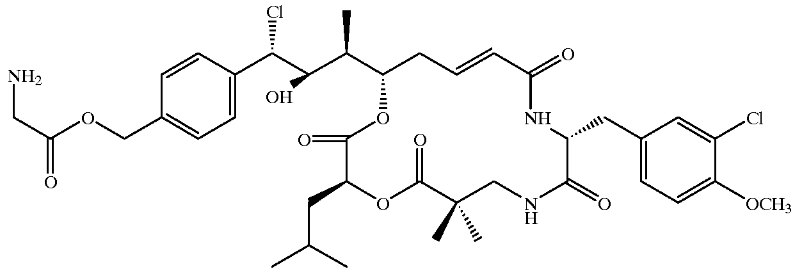

or a pharmaceutically acceptable salt thereof.

23. A method according to claim 22 wherein said compound is Compound I.

24. A method according to claim 22 wherein said compound is Compound II.

25. A method according to claim 22 wherein said compound is Compound III.

26. A method according to claim 22 wherein said compound is Compound IV.

27. A method according to claim 22 wherein said compound is Compound V.

28. A method for controlling a parasite infection comprising administering a therapeutically effective amount of a compound selected from the group consisting of Compound I, Compound II, Compound III, Compound IV and Compound V:

I

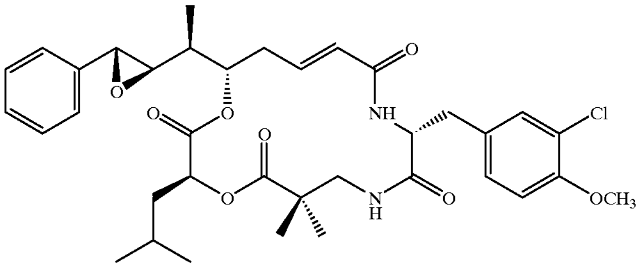

Compound II:

II

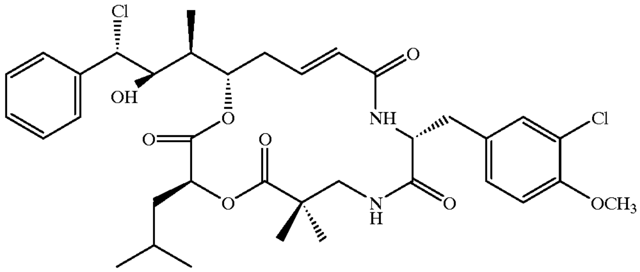

-continued

Compound III:

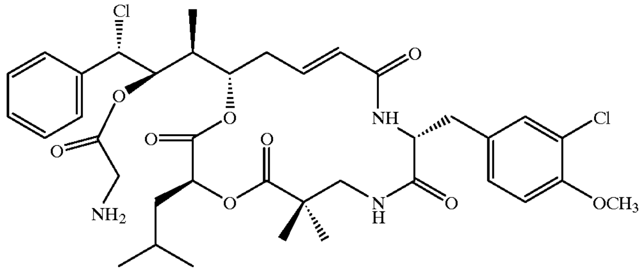

III

Compound IV:

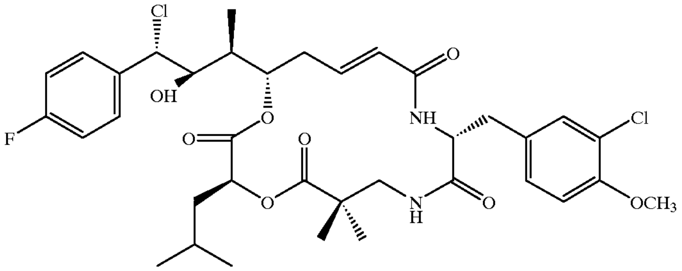

IV

Compound V:

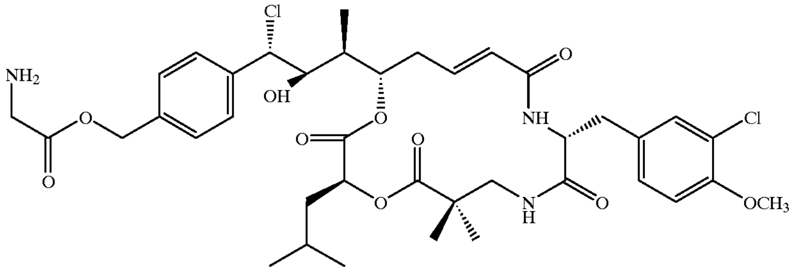

V or a pharmaceutically acceptable salt thereof.

29. A method according to claim 28 wherein said compound is Compound I.

30. A method according to claim 28 wherein said compound is Compound I.

31. A method according to claim 28 wherein said compound is Compound III.

32. A method according to claim 28 wherein said compound is Compound IV.

33. A method according to claim 28 wherein said compound is Compound V.

* * * * *